(12) United States Patent
Kelson et al.

(10) Patent No.: US 11,666,781 B2
(45) Date of Patent: *Jun. 6, 2023

(54) TREATMENT PLANNING FOR ALPHA PARTICLE RADIOTHERAPY

(71) Applicant: Alpha Tau Medical Ltd., Jerusalem (IL)

(72) Inventors: Itzhak Kelson, Tel Aviv (IL); Lior Arazi, Tel Aviv (IL); Amnon Gat, Matan (IL); Guy Heger, Ramat Gan (IL)

(73) Assignee: ALPHA TAU MEDICAL LTD., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/497,937

(22) Filed: Oct. 10, 2021

(65) Prior Publication Data
US 2022/0219012 A1 Jul. 14, 2022

Related U.S. Application Data

(63) Continuation-in-part of application No. 17/141,251, filed on Jan. 5, 2021.

(51) Int. Cl.
*A61N 5/10* (2006.01)

(52) U.S. Cl.
CPC ......... *A61N 5/1031* (2013.01); *A61N 5/1001* (2013.01); *A61N 2005/1034* (2013.01); *A61N 2005/1087* (2013.01)

(58) Field of Classification Search
CPC .......... A61N 5/10; G16H 20/40; G16H 50/50; G16H 70/60; G16H 30/20
See application file for complete search history.

(56) References Cited

U.S. PATENT DOCUMENTS

| 8,834,837 B2 | 9/2014 | Kelson et al. |
| 8,894,969 B2 | 11/2014 | Kelson et al. |

(Continued)

FOREIGN PATENT DOCUMENTS

| WO | 2019161135 A1 | 8/2019 |
| WO | 2019235841 A1 | 12/2019 |

OTHER PUBLICATIONS

A Popovtzer, E Rosenfeld, R Ben-Hur, A Mizrachy, I Kelson, and Y Keisari. "A New Radiation Concept, Treatment of Squamous Cell Carcinoma by Alpha-radiation Based Brachytherapy (Alpha DaRT)". International Journal of Radiation Oncology*Biology*Physics, 2018, 102.3:e275. (Year: 2018) (Year: 2018).*

(Continued)

*Primary Examiner* — Christine H Matthews
*Assistant Examiner* — Joshua Daryl D Lannu
(74) *Attorney, Agent, or Firm* — Kligler & Associates Patent Attorneys Ltd

(57) ABSTRACT

Apparatus for planning a diffusing alpha-emitter radiation therapy (DaRT) treatment session. The apparatus includes an output interface and a memory configured with a plurality of tables which provide an accumulated measure of radiation over a specific time period, due to one or more types of DaRT radiotherapy sources which emit daughter radionuclides from the source, for a plurality of different distances and angles relative to the DaRT radiotherapy source. In addition, a processor is configured to receive a description of a layout of a plurality of DaRT radiotherapy sources in a tumor, to calculate a radiation dose distribution in the tumor responsive to the layout, using the tables in the memory, and to output feedback for the treatment responsive to the radiation dose distribution, through the output interface.

33 Claims, 9 Drawing Sheets

(56) References Cited

U.S. PATENT DOCUMENTS

| | | |
|---|---|---|
| 2002/0046010 A1 | 4/2002 | Wessol et al. |
| 2007/0084474 A1 | 4/2007 | Rivard |
| 2009/0182187 A1 | 7/2009 | Chaswal et al. |
| 2011/0184283 A1 | 7/2011 | Rivard |
| 2013/0165732 A1 | 6/2013 | Sgouros et al. |
| 2014/0018607 A1* | 1/2014 | Maier .................. A61N 5/1039 600/8 |
| 2019/0099620 A1 | 4/2019 | Isola et al. |

OTHER PUBLICATIONS

International Application # PCT/IB2021/061607 Search Report dated Apr. 4, 2022.

Arazi, "Diffusing Alpha-Emitters Radiation Therapy: Theoretical and Experimental Dosimetry," Ph.D. Thesis, Raymond and Beverly Sackler Faculty of Exact Sciences, School of Physics and Astronomy, Tel Aviv University, pp. 1-285, Sep. 2008.

Arazi et al., "Treatment of Solid Tumors by Interstitial Release of Recoiling Short-Lived Alpha Emitters," Physics in Medicine and Biology, vol. 52, issue 16, pp. 5025-5042, Aug. 1, 2007.

Arazi et al., "The Treatment of Solid Tumors by Alpha Emitters Released from 224Ra-Loaded Sources—Internal Dosimetry Analysis," Physics in Medicine and Biology, vol. 55, issue 4, pp. 1203-1218, Feb. 2, 2010.

Arazi, "Diffusing Alpha-Emitters Radiation Therapy: Approximate Modeling of the Macroscopic Alpha Particle Dose of a Point Source," Physics in Medicine and Biology, vol. 65, issue 1, 24 pages, year 2020.

Nath et al., Recommendations of the AAPM Radiation Therapy Committee Task Group No. 43, Medical Physics, vol. 22, issue 2, pp. 209-234, Feb. 1995.

Rivard et al., "Update of AAPM Task Group No. 43 Report: a Revised AAPM Protocol for Brachytherapy Dose Calculations," Medical Physics, vol. 31, issue 3, pp. 633-674, Mar. 2004.

Popovtzer et al., "A New Radiation Concept, Treatment of Squamous Cell Carcinoma by Alpha-Radiation Based Brachytherapy (Alpha DaRT)," International Journal of Radiation Oncology—Biology—Physics, vol. 102, No. 3S, supplement 2018, p. E275, year 2018.

International Application # PCT/IB2021/050034 Search Report dated Apr. 29, 2021.

U.S. Appl. No. 17/141,251 Office Action dated Sep. 16, 2022.

* cited by examiner

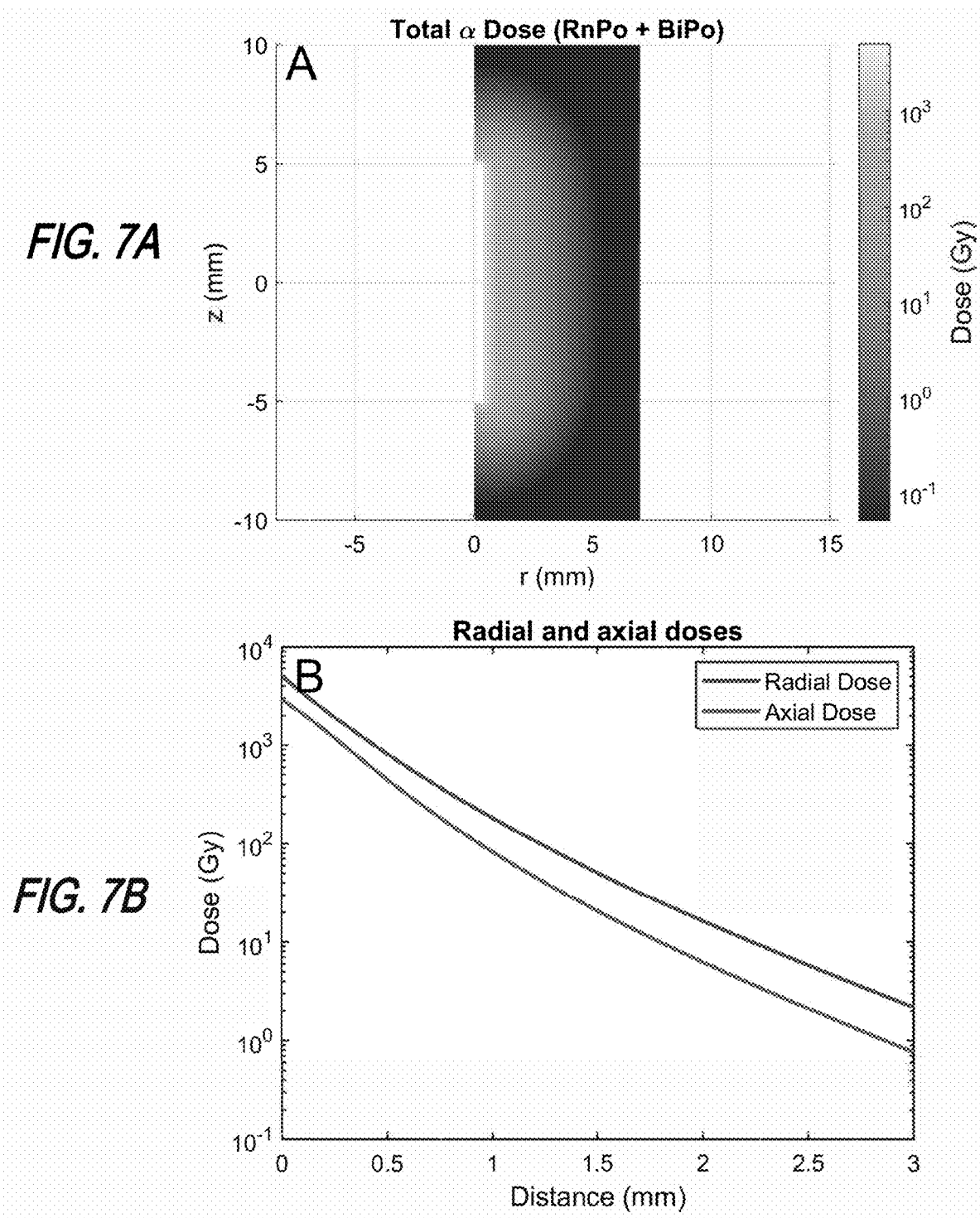

TREATMENT PLANNING FOR ALPHA PARTICLE RADIOTHERAPY

FIELD OF THE INVENTION

The present invention relates generally to radiotherapy and particularly to methods of selecting radiotherapy parameters.

BACKGROUND OF THE INVENTION

Alpha particles are a powerful means for radiotherapy of certain types of tumors, including malignant tumors. One type of alpha radiotherapy sources are diffusing alpha-emitter radiation therapy (DaRT) sources, also referred to herein as alpha-DaRT sources, loaded with radium-224 atoms, which have a half-life which is not too long and not too short for therapeutic purposes.

U.S. Pat. No. 8,834,837 to Kelson describes a method of DaRT treatment.

In order for treatment of a tumor to be effective, brachytherapy seeds employed in the treatment should release a sufficient number of particles to destroy the tumor. On the other hand, the seeds should not release an overdose of particles, as that could damage healthy tissue of the patient.

US patent publication 2013/0165732 to Sgouros et al. describes a computerized system for determining an optimum amount of radiopharmaceutical therapy (RPT) to administer.

The TG-43 publication (Recommendations of the AAPM Radiation Therapy Committee Task Group No. 43, Med. Phys. 22: 209-234) defines necessary physical quantities (e.g., air kerma strength, radial dose function, anisotropy function, dose rate constant, and the like) for the calculation of quantitative dosimetric data, for various interstitial brachytherapy sources.

US patent publication 2019/0099620 suggests adapting a radiotherapy treatment plan on the basis of a set of influence parameters quantifying an influence of the radiation on the target region per unity intensity emission in accordance with an anatomical configuration of the target region.

US patent publication 2011/0184283 describes brachytherapy treatment planning systems (TPS) which use Monte Carlo methods and calculate dose to a specific tissue type.

SUMMARY OF THE INVENTION

An aspect of some embodiments of the invention relates to a method for selecting parameters of a diffusing alpha-emitter radiation therapy, comprising calculating a dose distribution for a tumor radiotherapy, and adjusting the parameters based on the dose distribution.

There is therefore provided in accordance with embodiments of the present invention, apparatus for planning a diffusing alpha-emitter radiation therapy (DaRT) treatment session, comprising an output interface, a memory configured with a plurality of tables which provide an accumulated measure of radiation over a specific time period, due to one or more types of DaRT radiotherapy sources which emit daughter radionuclides from the source, for a plurality of different distances and angles relative to the DaRT radiotherapy source and a processor configured to receive a description of a layout of a plurality of DaRT radiotherapy sources in a tumor, to calculate a radiation dose distribution in the tumor responsive to the layout, using the tables in the memory, and to output feedback for the treatment responsive to the radiation dose distribution, through the output interface.

Optionally, the memory is configured with a plurality of tables for different time periods for a single source type, and wherein the processor is configured to determine a treatment duration of the layout, and to select tables to be used in calculating the radiation dose distribution responsive to the treatment duration. Optionally, the memory is configured with a plurality of tables for sources of a single source type in different zones of the tumor, and wherein the processor is configured to select tables to be used in calculating the radiation dose from each source in the layout, responsive to the zone in which the source is located. Optionally, the processor determines the zone in which a source is located responsive to a distance between the source and an edge of the tumor. Optionally, the processor is configured to identify areas of the tumor for which the dose is below a threshold and to suggest changes to the layout which bring the radiation dose in the identified areas to above the threshold.

Optionally, the processor is configured to repeat the calculation of radiation dose distribution for a plurality of different treatment durations and to select one of the durations responsive to the calculations. Optionally, the accumulated measure of radiation provided by the table comprises an accumulated radiation dose due only to alpha radiation.

Optionally, the accumulated measure of radiation provided by the table comprises an accumulated radiation dose due to alpha radiation and one or more of electron and photon radiation.

Optionally, the accumulated measure of radiation provided by the table comprises one or more number densities of radionuclides.

There is further provided in accordance with embodiments of the present invention, a method of planning a radiotherapy treatment session, comprising receiving, by a processor, a description of a layout of a plurality of DaRT radiotherapy sources in a tumor, calculating, by the processor, a radiation dose distribution in the tumor responsive to the layout, using tables which provide an accumulated measure of radiation over a specific time period, due to one or more types of DaRT radiotherapy sources which emit daughter radionuclides from the source, for a plurality of different distances and angles relative to the DaRT radiotherapy source, and outputting from the processor feedback for the treatment responsive to the radiation dose distribution.

Optionally, calculating the radiation dose distribution comprises determining a treatment duration of the layout, and select tables to be used in calculating the radiation dose distribution responsive to the treatment duration. Optionally, calculating the radiation dose distribution comprises selecting tables to be used in calculating the radiation dose from each source in the layout, responsive to a zone of the tumor in which the source is located. Optionally, the method includes repeating the calculation of radiation dose distribution for a plurality of different treatment durations and selecting one of the durations responsive to the calculations.

There is further provided in accordance with embodiments of the present invention, a method of planning a radiotherapy treatment session, comprising receiving, by a processor, a plurality of parameters of tissue of a tumor requiring radiotherapy, receiving, by the processor, an indication of a layout of diffusing alpha-emitter radiation therapy (DaRT) sources to be placed in the tumor, calculating a distribution of radon-220, lead-212 and bismuth-212 radionuclides in the tumor, responsive to the layout of sources, determining a distribution of a dose resulting from alpha radiation emitted in the tumor responsive to the calculated distribution, determining an electron and a photon radiation dose distribution in the tumor, responsive to the sources; and setting one or more parameters of the radiotherapy treatment session responsive to the determined distributions of the alpha, electron and photon radiation.

Optionally, calculating the distribution of radon-220, lead-212 and bismuth-212 is performed as a function of diffusion coefficients of radon-220 and lead-212 in the tumor.

Optionally, calculating the distribution of radon-220, lead-212 and bismuth-212 is performed by solving a migration equation of lead-212 including a leakage factor which is a product of the concentration of lead-212 and a constant. Optionally, calculating the distribution of the radionuclides comprises calculating a distribution of the radionuclides for a single source and summing the distributions of the sources in the layout.

Optionally, the setting one or more parameters of the radiotherapy treatment session comprises selecting an activity of the sources. Optionally, the setting one or more parameters of the radiotherapy treatment session comprises adjusting the layout of the sources. Optionally, calculating the distribution of radon-220, Lead-212 and bismuth-212 in the tumor and determining the distribution of alpha radiation comprises preparing in advance tables of radiation distributions for a plurality of different tumor types and calculating the distribution of alpha radiation by summing values matching the layout from one of the tables. Optionally, preparing in advance tables of radiation distributions comprises preparing for each of the tumor types, a plurality of tables for respective treatment durations.

Optionally, the treatment durations for which the tables are prepared, are unevenly distributed over the duration of the effectiveness of the sources of the layout. Optionally, calculating the distribution of radionuclides in the tumor and determining the distribution of alpha radiation comprises repeating the determination for a plurality of different durations, and wherein setting one or more parameters of the radiotherapy treatment session comprises selecting a duration of the treatment responsive to the repeated determinations.

Optionally, receiving the indication of the layout comprises receiving an image of the tumor with the sources therein and determining the locations of the sources in the tumor responsive to the image. Optionally, determining the electron and the photon radiation dose distribution, is performed in a manner ignoring the distribution of radon-220, Lead-212 and bismuth-212 in the tumor. Optionally, calculating the distribution of radon-220, lead-212 and bismuth-212 radionuclides comprises calculating based on at least one equation which depends and a diffusion coefficient of lead-212, and wherein the value of the diffusion coefficient of lead-212 is calculated as a function of a diffusion length of lead-212. Optionally, the diffusion length of lead-212 is assigned a value in the range of 0.2-0.4 millimeters.

Optionally, the diffusion length of lead-212 is assigned a value dependent on the tissue type of the tumor.

Optionally, calculating the distribution comprises solving equations numerically using finite elements. Optionally, calculating the distribution comprises determining a finite element two-dimensional time-dependent solution. Optionally, calculating the distribution comprises solving equations numerically using finite elements, with boundary conditions for each of the sources both on an outer surface of the source and on an axis of the source. Optionally, calculating the distribution comprises solving equations numerically using finite elements for a respective cylindrical domain surrounding each of the sources, wherein outside the cylindrical domain the number density is set to zero.

BRIEF DESCRIPTION OF THE DRAWINGS

FIG. 7A is a graph showing total alpha dose accumulated over 40 days of treatment by a DaRT seed with initial activity of 3 µCi $^{224}$Ra, a seed radius of 0.35 mm and a seed length of 10 mm;

FIG. 7B is a graph showing total alpha dose as a function of the distance from the seed age along r in the mid plane and along z on the seed axis;

DETAILED DESCRIPTION OF EMBODIMENTS

An aspect of some embodiments of the present invention relate to the use of pre-calculated tables of the radiation distribution due to a radiotherapy source, in calculating an estimated radiation amount resulting from an alpha-DaRT source, which emits daughter radionuclides into a treated tumor. The tables provide, for a plurality of positions relative to the source, an accumulated radiation dose at the position.

In some embodiments, separate tables, or table entries, are used for different time periods of radiotherapy treatment.

In some embodiments, separate tables are provided for different areas within the tumor, for example according to distance from the edge of the tumor.

Using tables which indicate the accumulated dose over a treatment period, overcomes the problem that the spatial distribution of radionuclides is time dependent and cannot be factorized into a time dependent and spatial dependent component.

In addition, use of the dose in the tables avoids the problem that for DaRT the dose rate at t=0 is 0, increases with time and then decreases.

Figure 1:
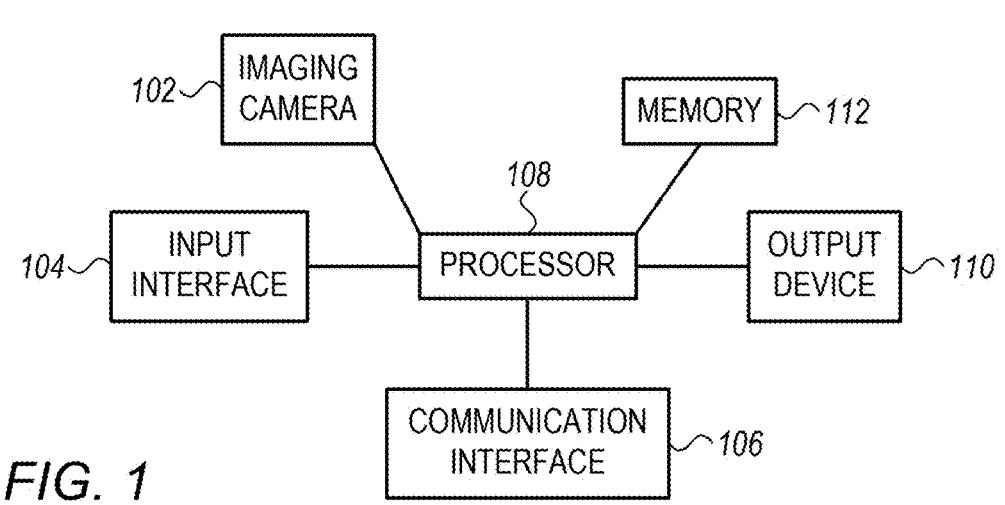
FIG. 1 is a schematic illustration of a system for planning a radiotherapy treatment, in accordance with an embodiment of the present invention.

FIG. 1 is a schematic illustration of a system 100 for planning a radiotherapy treatment, in accordance with an embodiment of the present invention. The treatment generally includes implantation of a plurality of sources in a tumor which is to be destroyed. The sources, also known as "seeds", generally comprise a base coated by radium-224 as described, for example, in U.S. Pat. No. 8,894,969, which is incorporated herein by reference. The base may have any suitable shape, such as a thin cylinder shape.

System 100 comprises an imaging camera 102 which acquires images of tumors requiring radiotherapy. In addition, system 100 includes an input interface 104, such as a keyboard and/or mouse, for receiving input from a human operator, such as a physician.

Alternatively or additionally, system 100 comprises a communication interface 106 for receiving instructions and/or data from a remote computer or human operator. System 100 further comprises a processor 108 configured to generate a layout plan of radiotherapy sources in the tumor. Processor 108 is further configured to estimate the radiation dose expected to reach each of the points in the tumor, and accordingly to provide an output to the human operator through an output device 110, such as a computer screen.

Processor 108 is coupled to a memory 112 which preferably stores tables of radiation doses as a function of distance, and optionally also angle, from the source. The tables are calculated in advance for different types of sources and parameters of the tumor tissue, as discussed hereinbelow.

Figure 2:
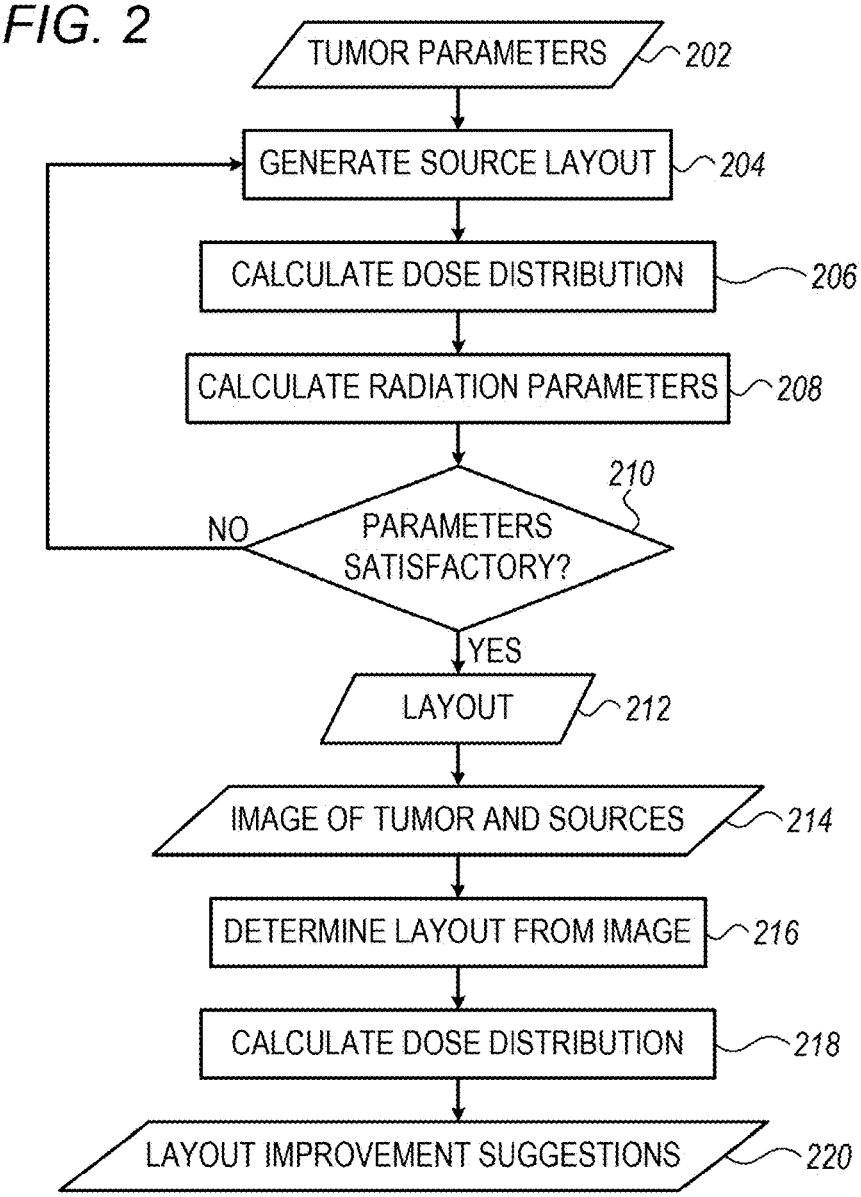
FIG. 2 is a flowchart of acts of a method of calculating a dose distribution for a tumor radiotherapy, in accordance with an embodiment of the invention.

FIG. 2 is a flowchart of acts performed by system 100, in accordance with an embodiment of the invention. System 100 receives (202) input on the tumor and a layout of radiotherapy sources for the tumor is generated (204). The layout optionally includes, in addition to relative positions of the sources, information on the sources (e.g., the activity level of the sources) and a time of treatment.

Processor 108 calculates (206) a dose distribution of the radiation from the sources of the layout and/or calculates (208) any other parameters of the radiation of the sources, such as a dose volume histogram and/or a dose-rate distribution. In some embodiments, a determination (210) is made as to whether the dose distribution and/or other parameters are satisfactory, and if not satisfactory, a new layout is generated (204) and the calculation of the dose distribution and/or the other parameters of the radiation are repeated for the new layout. The generation (204) of layouts and calculation of dose distribution (206) and/or the other parameters (208) is optionally repeated until a suitable layout is identified and provided (212) for insertion of the sources into the tumor.

In some embodiments, the determination (210) as to whether the dose distribution and/or other parameters are satisfactory, and the generation of the new layout are performed by a human operator. Alternatively, processor 108 automatically determines (210) whether the dose distribution is sufficient, for example by determining areas of the tumor where the radiation is below a first threshold. The first threshold is optionally selected responsive to the type of the tumor, for example the nucleus size of the cells of the tumor. In some embodiments, processor 108 automatically determines a percentage of the tumor to which the radiation dose is above the first threshold and compares this percentage to a second threshold. The generation (204) of the new layout is optionally performed automatically by moving sources from areas where the radiation is substantially above the first threshold, to areas where the radiation dose is below the first threshold. Alternatively or additionally, the automatic generation of the new layout is performed by adding additional sources.

In some embodiments, after the sources are inserted into the tumor, an image of the tumor with the sources is acquired (214) and the actual layout of sources in the tumor is determined (216). Processor 108 then optionally calculates (218) a dose distribution of the radiation from the sources of the actual layout and if necessary provides (220) suggestions for improvement of the layout.

The suggestions (220) for improvement of the layout and the generation (204) of the new layout, may include adding sources to be inserted to the tumor, removal of unnecessary sources, moving one or more sources in the layout (e.g., changing the spacings between sources), changing the activity and/or desorption probability of one or more of the sources and/or changing the types or sizes of the sources.

In some embodiments, the layout is generated (204) automatically by processor 108 by distributing sources throughout the tumor in a default spacing for the specific tumor type. Alternatively or additionally, the layout is generated with a spacing indicated by the human operator. Further alternatively or additionally, a human operator indicates locations of the sources through input interface 104, on a displayed image of the tumor. The layout optionally also includes an indication of one or more properties of the sources used in the layout, such as the length of the sources and/or their activity level (i.e., the amount of radioactive atoms on the sources). The information on the sources may be provided by a human user or may be selected by processor 108 automatically, for example based on default values, or based on a code number provided by the human operator. In some embodiments, processor 108 determines the properties of the sources from an image of the tumor, with the sources therein, in cases in which the analysis is of sources already implanted. The sources may include, in these embodiments, markings of their type and/or properties, which are easily determinable from images of the tumor.

The information on the layout optionally also includes a duration for which the analysis is performed, for example, the amount of time the sources are planned to be in the tumor, or an amount of time for which the sources were in the patient if the analysis is performed after the treatment was completed. In some embodiments of the invention, the calculation is performed for a plurality of different durations, in order to select a duration most suitable for the treatment. For example, the calculation may be performed during the treatment to determine when to remove the sources.

The calculation (206) of the dose distribution is based, in some embodiments, on pre-generated tables stored in memory 112. The calculation (206) optionally includes selecting one of the tables in memory 112, responsive to the type of the tissue of the tumor and the type of the sources used in the layout. For each type of tissue, the tables are calculated in advance as described below with reference to FIG. 3. Each table optionally indicates, for a plurality of locations relative to the source type of the table, an amount of radiation reaching the location, per unit of activity of the source. The locations are optionally designated by an angle (θ) and distance (r) from a center of the source. The table includes, for example, 90 rows representing possible angles in a granularity of 2° in the range of 0°-180°, and 100 columns of distances from 0 to 10 millimeters in a granularity of 0.1 millimeter. These numbers of rows and columns are provided by way of example and larger or smaller tables with coarser or finer granularities are also to be considered in the scope of the present invention. For example, the table may include 180 rows for a 1° granularity. In some embodiments, dose values in the tables are provided in units of gray. In other embodiments, the values in the table are of dose per initial release rate of radon, for example in units of gray to micro-Curie.

The tables described herein may be stored in memory 112 in any suitable data structure. Each table may be stored, for example, in a single array, or in a plurality of arrays. Each of the tables may be stored separately, or a plurality of tables may be stored together as a single table, of a larger dimension.

In calculation (206) of the dose distribution, for each location of interest (e.g., the locations in the tumor, and possibly also adjacent the tumor), processor 108 checks the table for the radiation dose received from each of the sources per unit activity of the source, and multiplies this value by the activity of the source. These values are summed to provide the total radiation dose reaching the point. Alternatively to multiplying by the activity of the sources, the doses from the table are multiplied by the release rate of radon from the source.

In some embodiments, in which all the sources have the same activity, the multiplication by the activity or by the release rate of radon of the sources may be performed after the summation.

Alternatively or additionally, separate tables are provided for each activity level (or release rate of radon), and the tables provide values of activity or release rate of radon, such that the multiplication is not required.

In some embodiments, for each tissue type, a plurality of tables are provided for different treatment durations. For example, tables are optionally provided for a span of equally distanced durations with a granularity of one day or two days. Alternatively, the tables are prepared for unevenly distributed durations, for which the calculated doses are sufficiently different to warrant an additional table. In selecting the table to be used for a specific source, the duration of the treatment is also considered. In some embodiments, when a treatment duration is between the durations of two different tables, the values from both tables are retrieved and the actual value is calculated from the table values by interpolation. Alternatively, in cases in which the treatment is expected to always be for a relatively long duration, a single table of a long duration, greater than several half-lives of radium-224, is used.

In other embodiments, the tables indicate other parameters from which the dose may be calculated relatively easily. For example, the tables provide, in some embodiments, a number of accumulated decays of two or more radionuclides involved in the treatment, for each of the positions relative to the source. The radiation dose is calculated from the values in the table by first determining the number of accumulated decays of the radionuclides involved in the treatment not included in the table, and then calculating the dose from the numbers of accumulated decays. The calculation of the radiation dose from the numbers of accumulated decays may be performed before or after the summation of the effect of all the sources in the layout. Optionally, the two or more radionuclides whose number of accumulated decays are included in the tables are radon-220 and bismuth-212. Alternatively to radon-220, the number of accumulated decays of polonium-216 is given. Further alternatively or additionally, instead of for bismuth-212, the number of accumulated decays in the tables may be of lead-212, polonium-212 and/or thallium-208. In some embodiments, the table may give the number of accumulated decays for more than two or even more than three of the radionuclides, possibly even of all the radionuclides involved in the treatment.

In some embodiments, the type of the tumor is determined based on clinical and/or histopathological observations, such as an analysis of a portion of the tumor taken in a biopsy. The type of the tumor is selected, for example, from a list including squamous cell carcinoma, basal cell carcinoma, glioblastoma, sarcoma, pancreatic cancer, lung cancer, prostate cancer, breast cancer and colon cancer. This list of tumor types is provided merely as one example and tables may be prepared for larger or smaller lists of tumor types including all or some of the above listed types and/or other types not listed here.

Figure 3:
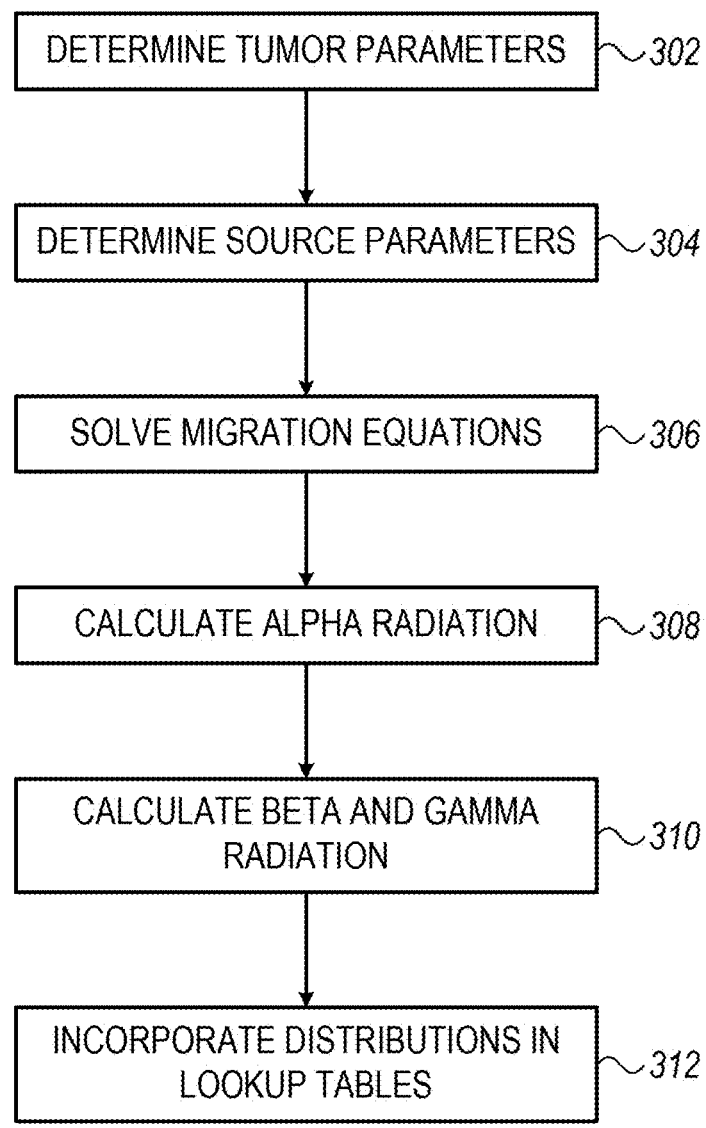
FIG. 3 is a schematic illustration of acts performed in generating the tables in memory, in accordance with an embodiment of the invention.

FIG. 3 is a schematic illustration of acts performed in generating the tables in memory 112, in accordance with an embodiment of the invention. The method optionally includes determining (302) one or more tissue specific parameters which represent the diffusion of radioactive isotopes from the sources in tumors of different types of cancers to be treated.

Optionally, the parameters include diffusion coefficients $D_{Rn}$, $D_{Pb}$ and $D_{Bi}$ of the isotopes radon-220 ($^{220}$Rn), lead-212 ($^{212}$Pb) and bismuth-212 ($^{212}$Bi), respectively, in the different tumor types. Optionally, the diffusion coefficients $D_{Rn}$, $D_{Pb}$ and $D_{Bi}$, are measured using methods known in the art, such as described in Lior Arazi, "Diffusing Alpha-Emitters Radiation Therapy: Theoretical and Experimental Dosimetry", Thesis submitted to the senate of Tel Aviv University, September 2008, the disclosure of which is incorporated herein by reference, and/or in Lior Arazi et al., "Treatment of solid tumors by interstitial release of recoiling short-lived alpha emitters", Physics in Medicine & Biology, 2007, the disclosure of which is incorporated herein by reference.

In some embodiments, the diffusion coefficients $D_{Rn}$, $D_{Pb}$ and $D_{Bi}$, are measured in mice or other test animals. While such measurements may not be totally accurate, due, for example, to convective effects, applicant has determined that even when these inaccuracies are ignored, the calculations achieve suitable results.

The tissue specific parameters optionally further include the parameters $\alpha_{Pb}$ and $\alpha_{Bi}$ which represent a leakage rate (assumed to be uniform throughout the tumor) of lead-212 and Bi-212 respectively due to leakage through the blood from the tumor. The leakage rate parameters $\alpha_{Pb}$ and $\alpha_{Bi}$ are optionally determined such that the mean leakage times (average time for $^{212}$Pb and $^{212}$Bi to leave the tumor through the blood) are $1/\alpha_{Pb}$ and $1/\alpha_{Bi}$.

In some embodiments, the value of $\alpha_{Pb}$ is determined from measured values of the lead-212 leakage probability. The lead-212 leakage probability is measured using any suitable method known in the art, such as measurement in mice as described in the above mentioned article of Lior Arazi et al., "Treatment of solid tumors by interstitial release of recoiling short-lived alpha emitters", Physics in Medicine & Biology, 2007. Alternatively or additionally, the value of $\alpha_{Pb}$ is inferred from activity measurements in blood and/or urine of human patients using a biokinetic model, for example as described in Lior Arazi et al., "The Treatment Of Solid Tumors By Alpha Emitters Released From $^{224}$Ra-Loaded Sources—Internal Dosimetry Analysis", Physics in Medicine and Biology, February 2010, the disclosure of which is incorporated herein by reference in its entirety.

Preclinical data gathered from samples of DaRT-treated tumors, indicated that $^{212}$Bi leakage from the tumor, independently of the leakage of $^{212}$Pb, is a small effect, which implies that $\alpha_{Bi} \ll \lambda_{Bi}$ (where $\lambda_{Bi}$ is the decay rate constant of bismuth-212). In addition, $^{212}$Bi was found to be in local transit equilibrium with $^{212}$Pb, which, in turn implies that $D_{Bi} \lesssim 0.2 D_{Pb}$. Accordingly, in some embodiments, it is assumed that $\alpha_{Bi} = 0$ and $D_{Bi} = 0.1 D_{Pb}$. Alternatively, $\alpha_{Bi}$ is inferred from measurements in mice-based experiments in which the ratio of the activities of Bi-212 and lead-212 is measured in small samples. Further alternatively, $\alpha_{Bi}$ is set to a product of $\alpha_{Bi}$ and a constant k smaller than 1, smaller than 0.25 or even not greater than 0.2, for example 0.2 or 0.1. $D_{Bi}$ is set in some embodiments as a product of $D_{Pb}$ and a constant $k_2$, where typically $k_2 < 1$.

The method further includes determining (304) parameters which represent the radiotherapy source. In some embodiments, the source is represented by: $\Gamma_{Ra}^{src}(0)$, which is the initial $^{224}$Ra activity of the source, $P_{des}(Rn)$ which is an $^{220}$Rn desorption probability from the source (i.e., the probability that a $^{220}$Rn is emitted from the source when $^{224}$Ra decays) and $P_{des}^{eff}(Pb)$ which is an effective desorption probability of $^{212}$Pb from the source, due to any of the possible $^{212}$Pb release paths from the source. Optionally, $P_{des}^{eff}(Pb)$ takes into account two $^{216}$Po channels, as well as creation of $^{212}$Pb outside of the source following the emission of $^{220}$Rn from the surface of the source. These parameters are determined using any suitable method known in the art, such as any of the methods described in the above mentioned article: Lior Arazi, "Diffusing alpha-emitters radiation therapy: approximate modeling of the macroscopic alpha particle dose of a point source", Physics in Medicine and Biology, 2020.

Using the tissue specific parameters and the source parameters, equations of migration of each of the isotopes $^{220}$Rn, $^{212}$Pb and $^{212}$Bi, resulting from the source, are solved (306) to determine the spatial distributions of the isotopes $n_{Rn}(r,t)$, $n_{Pb}(r,t)$ and $n_{Bi}(r,t)$, as a function of time t and position r relative to the source. Generally, the position r is a three-dimensional vector, but in some cases, for simplicity, a simpler measure of position is used, for example based on symmetry considerations. Optionally, due to the short half-lives of $^{216}$Po, $^{212}$Po and $^{208}$Tl, these isotopes are assumed to be in local transit and/or secular equilibrium with their parent isotopes and do not require separate equations to calculate their spatial distributions.

The resulting alpha radiation dose from the determined spatial distributions of the isotopes is calculated (308). In addition, the electron (beta, Auger, conversion electron) and photon (gamma, x-ray) radiation dose from the source is calculated (310) using any suitable method known in the art. The calculated alpha, electron and photon radiation dose distributions $D(r,\theta,t)$ are optionally incorporated (312) into lookup tables for each set of parameters of tumor type and source type. Here, assuming axial symmetry, r designates the radial distance of the point of interest from the source center and $\theta$ designates the angle between the line connecting the point of interest to the source center and the source axis.

Migration Equations

In some embodiments, the radon migration equation (also referred to as a transport equation) is given by:

$$\frac{\partial n_{Rn}}{\partial t} + \nabla \cdot j_{Rn} = S_{Rn} - \lambda_{Rn} n_{Rn} \qquad (1)$$

Where $$\frac{\partial n_{Rn}}{\partial t}$$

is a rate of change of the amount of radon, $n_{Rn}(r,t)$ is the local concentration (number density) of $^{220}$Rn atoms (in units of cm$^{-3}$), $S_{Rn}(r,t)$ is the $^{220}$Rn source term (i.e., the amount of radon released into the tissue due to the decay of $^{224}$Ra) (in units of cm$^{-3}$ s$^{-1}$), and $\lambda_{Rn}$ is the decay rate constant $\lambda_{Rn} = \ln(2/\tau_{1/2})$, where $\tau_{1/2}$ is the half-life constant of radon-220. Note that if $^{224}$Ra is completely confined to the source $S_{Rn}(r,t)=0$ in the tumor volume and the source term is replaced by a suitable boundary condition on the source surface describing the flux of emitted $^{220}$Rn atoms. The current density $j_{Rn}(r,t)$ is the net vector flux of 220Rn atoms (in units of cm$^{-2}$ s$^{-1}$).

In the most general case, $j_{Rn}(r,t)$ is composed of both diffusive and convective terms:

$$j_{Rn}(r,t) = -D_{Rn}(r,t)\nabla n_{Rn}(r,t) + n_{Rn}(r,t)v(r,t) \qquad (2)$$

v(r,t) is a vector field describing both vascular and interstitial flow inside the tumor.

The Pb migration equation is optionally:

$$\frac{\partial n_{Pb}}{\partial t} + \nabla \cdot j_{Pb} = S_{Pb} - \lambda_{Pb} n_{Pb} \qquad (3)$$

where $$j_{Pb}(r, t) = -D_{Pb}(r, t)\nabla n_{Pb}(r, t) + n_{Pb}(r, t)v(r, t) \qquad (4)$$

The transport equation relating to the total $^{212}$Bi number density is optionally:

$$\frac{\partial n_{Bi}}{\partial t} + \nabla \cdot j_{Bi} = S_{Bi} - \lambda_{Bi} n_{Bi} \qquad (5)$$

where:

$$j_{Bi}(r, t) = -D_{Bi}(r, t)\nabla n_{Bi}(r, t) + n_{Bi}(r, t)v(r, t) \qquad (6)$$

If $^{224}$Ra of a meaningful amount is present in the tumor away from the source, its number density $n_{Ra}(r,t)$ can be found by solving a separate transport equation, and then used as a volumetric source term for $^{220}$Rn, with $s_{Rn}(r,t) = \lambda_{Ra} n_{Ra}(r,t)$.

The source terms $s_{Rn}(r,t)$ and $s_{Pb}(r,t)$ are optionally determined based on the given physical arrangement of the sources inside the tumor and with the appropriate flux boundary conditions on the source surfaces.

The above equations are solved (306) using any suitable method known in the art, such as Monte Carlo simulation describing the stochastic motion of $^{220}$Rn, $^{212}$Pb and $^{212}$Bi, or numerically using finite elements (for any source geometry, with appropriate boundary conditions). One method of numerically solving the equations using finite elements is described in the appendix to this application. These solution methods are required if one considers the tumor as a heterogenic, and possibly time-dependent medium, where the diffusion coefficients and velocity field depend on space and time. Alternatively, approximate solutions can be obtained if the tumor is modeled as a homogeneous, isotropic, and time-independent medium. In this case, in addition to the solution methods mentioned above, one can also solve the transport equations approximately using closed-form expressions for simple geometries, such as the ideal point source, infinite line source or infinite cylinder, and/or infinite planar source. An example solution which may be used is described in Lior Arazi, "Diffusing alpha-emitters radiation therapy: approximate modeling of the macroscopic alpha particle dose of a point source", Physics in Medicine and Biology, 2020, the disclosure of which is incorporated herein by reference.

In some embodiments, the equations are solved by first preparing solutions for point sources, and then summing the effects of the point sources forming the actual geometries of the sources.

For a point source of $^{224}$Ra, the $^{220}$Rn source term is optionally:

$$s_{Rn}(r,t)=P_{des}(Rn)\Gamma_{Ra}^{src}(0)e^{-\lambda_{Ra}t}\delta(r) \quad (7)$$

where r is the radial distance from the source. $\Gamma_{Ra}^{src}(0)$ is the initial $^{224}$Ra activity (t=0 at the time of the procedure), which decays exponentially as $e^{-\lambda_{Ra}t}$; $P_{des}$(Rn) is the $^{220}$Rn desorption probability from the source (i.e., the probability that a $^{220}$Rn is emitted from the source when $^{224}$Ra decays), and $\delta(r)$ is the Dirac delta function.

The source term for $^{212}$Pb is optionally:

$$s_{Pb}(r,t)=\lambda_{Rn}n_{Rn}+[P_{des}^{eff}(Pb)-P_{des}(Rn)]\Gamma_{Ra}^{src}(0)e^{-\lambda_{Ra}t}\delta(r) \quad (8)$$

The first term represents the local creation of $^{212}$Pb by the decay of $^{220}$Rn through $^{216}$Po away from the source. The second term represents the emission of $^{212}$Pb from the source either by direct recoil, when $^{216}$Po decays on the source, or in the immediate vicinity of the source when $^{216}$Po which has previously recoiled out of the source decays. Note that $P_{des}^{eff}$(Pb) is the effective desorption probability of $^{22}$Pb from the source which includes, in addition to two $^{216}$Po decay channels, also the creation of $^{212}$Pb outside of the source following the emission of $^{220}$Rn from the surface of the source. Since the contribution of $^{220}$Rn is already taken care of by the first term, $\lambda_{Rn}n_{Rn}$, in the second term we use the difference $P_{des}^{eff}$(Pb)–$P_{des}$(Rn).

It is optionally assumed that $^{212}$Bi enters the tumor only through decay of $^{212}$Pb away from the source and therefore the $^{212}$Bi source term in eq. (3) is:

$$s_{Bi}(r,t)=\lambda_{Pb}n_{Pb}(r,t) \quad (9)$$

In some embodiments, to cover diffusion of bismuth-212 from the source, when a source which allows such diffusion is used, a suitable boundary condition is added on the source. Alternatively, for an ideal point source, a Dirac delta function term can be employed for bismuth-212, as used above for radon-220 and lead-212.

In some embodiments, the equations are simplified to reduce the complexity of their solution, based on one or more of the following assumptions:

The tumor medium is homogenous, isotropic and time-independent. The diffusion and leakage rate coefficients are constant in space and time.

$^{224}$Ra daughter migration inside the tumor is predominantly diffusive. Vascular convection by the tortuous capillaries is characterized by a short correlation length (relative to therapeutically significant distances) and is therefore assumed to be in random directions. Thus, it can be incorporated into an effective diffusion coefficient.

The sources are assumed to remain fixed in place throughout the treatment.

All sources are the same: same length, same activity, same desorption probabilities.

$^{220}$Rn decays entirely inside the tumor.

Interstitial convection is neglected.

$^{212}$Pb migration can be described using a single effective diffusion coefficient representing the average over all $^{212}$Pb molecular species.

$^{212}$Pb atoms reaching major blood vessels are trapped in red blood cells (RBCs) and quickly cleared from the tumor. This process is described by a uniform volumetric sink term. The finite clearance rate reflects the time it takes migrating $^{212}$Pb atoms to reach such traps.

Since the short-lived $^{220}$Rn atoms are free to diffuse with no chemical interaction through blood vessels and RBCs, the equation for $^{220}$Rn does not include a sink term (i.e. blood vessels do not act as traps for $^{220}$Rn). However, in some embodiments, in blood-rich regions of the tumor a similar sink term can be added also to the equation of $^{220}$Rn.

The diffusion equation for $^{212}$Bi includes a sink term. However, this is generally considered a second order effect.

Under this set of assumptions, the above equations may be simplified to:

$$\frac{\partial n_{Rn}}{\partial t} - D_{Rn}\nabla^2 n_{Rn} = S_{Rn} - \lambda_{Rn}n_{Rn} \quad (10)$$

$$\frac{\partial n_{Pb}}{\partial t} - D_{Pb}\nabla^2 n_{Pb} = S_{Pb} - \lambda_{Pb}n_{Pb} - \alpha_{Pb}n_{Pb} \quad (11)$$

$$\frac{\partial n_{Bi}}{\partial t} - D_{Bi}\nabla^2 n_{Bi} = S_{Bi} - \lambda_{Bi}n_{Bi} - \alpha_{Bi}n_{Bi} \quad (12)$$

In equations (10)-(12) $n_{Rn}$(r,t), $n_{Pb}$(r,t) and $n_{Bi}$(r,t) are the local time-dependent number densities of $^{220}$Rn, $^{212}$Pb and $^{212}$Bi throughout the tumor. $D_{Rn}$, $D_{Pb}$ and $D_{Bi}$ are the effective diffusion coefficients of the three isotopes, which are assumed to be independent of the position and time. $\lambda_{Rn}$, $\lambda_{Pb}$ and $\lambda_{Bi}$ are the respective decay rate constants. The $^{212}$Pb and $^{212}$Bi equations contain sink terms $\alpha_{Pb}n_{Pb}$ and $\alpha_{Bi}n_{Bi}$ describing $^{212}$Pb and $^{212}$Bi leakage (i.e., removal from the tumor) through the blood.

As mentioned above regarding the general equations (1), (3), (5), equations (10)-(12) are solved (306) using any suitable method known in the art, such as Monte Carlo simulation describing the stochastic motion of $^{220}$Rn, $^{212}$Pb and $^{212}$Bi, numerically using finite elements (for any source geometry, with appropriate boundary conditions), or approximately using closed-form expressions for simple geometries, such as the ideal point source, infinite line source or infinite cylinder, and/or infinite planar source.

In some embodiments, for simplicity, instead of solving migration equations for all three of $^{220}$Rn, $^{212}$Pb and $^{212}$Bi, one or more of the radionuclides is assumed to have a fixed distribution or a distribution dependent on one or more of the other radionuclides. For example, in one embodiment, the calculation of the dose is calculated based on the migration equation of $^{212}$Pb and the distribution of $^{220}$Rn is considered negligible and the distribution of $^{212}$Bi is assumed to be a fixed function of the $^{212}$Pb distribution. Alternatively, one solves the equations for $^{220}$Rn and $^{212}$Pb, and the $^{212}$Bi number density is assumed to be proportional to that of $^{212}$Pb (e.g., in transit or secular equilibrium).

Alpha Dose Calculation

The alpha particle dose from the time of the procedure to time t has two components: one arising from the alpha decays of $^{220}$Rn and $^{216}$Po (which follows immediately at essentially the same location, due to the 0.15 s half-life of $^{216}$Po), and one arising from the alpha decay of either $^{212}$Bi (with 36% branching) or $^{212}$Po (with 64% branching). The accumulated dose may be summarized by the following equations, which depend on the values of $n_{Rn}(r,t)$, $n_{Pb}(r,t)$ and $n_{Bi}(r,t)$ calculated in solving the migration equations:

$$Dose_\alpha(RnPo; r, t) = \frac{E_\alpha(RnPo)}{\rho} \int_0^t \lambda_{Rn} n_{Rn}(r, t') dt' \quad (13)$$

$$Dose_\alpha(BiPo; r, t) = \frac{E_\alpha(BiPo)}{\rho} \int_0^t \lambda_{Bi} n_{Bi}(r, t') dt' \quad (14)$$

$E_\alpha(RnPo)=(6.29+6.78)$ MeV$=13.07$ MeV$=2.09 \cdot 10^{-12}$ J is the sum of energies of the alpha particles emitted (essentially at the same location) by $^{220}$Rn and $^{216}$Po. $E_\alpha(BiPo)=7.80$ MeV$=1.25 \cdot 10^{-12}$ J is the average energy of the alpha particles emitted either by $^{212}$Bi or $^{212}$Po and $\rho$ is the tissue density (which, for all practical purposes, can be set to 1 g/cm$^3$). We define the asymptotic dose as the dose delivered from the time of the implanting of the sources in the tumor to infinity (in practice to ~5 half-lives of $^{224}$Ra):

$$Dose_\alpha^{asy}(RnPo; r) = \frac{E_\alpha(RnPo)}{\rho} \int_0^\infty \lambda_{Rn} n_{Rn}(r, t) dt \quad (15)$$

$$Dose_\alpha^{asy}(BiPo; r) = \frac{E_\alpha(BiPo)}{\rho} \int_0^\infty \lambda_{Bi} n_{Bi}(r, t) dt \quad (16)$$

In some embodiments, the equations are solved based on the assumption of a uniform temporal behavior of the number densities throughout the entire region surrounding the source. This assumption is referred to as "0D approximation".

The asymptotic dose contributed by $^{220}$Rn and $^{216}$Po under the 0D approximation for a point source is given by:

$$Dose_\alpha^{asy,0D}(RnPo; r) = \frac{\lambda_{Rn} P_{des}(Rn) \Gamma_{Ra}^{STC}(0) E_\alpha(RnPo)}{4\pi \rho D_{Rn}} \frac{e^{-r/L_{Rn}}}{r} \tau_{Ra} \quad (17)$$

where $\tau_{Ra}=1/\lambda_{Ra}$ is the mean lifetime of $^{224}$Ra. To calculate an approximate dose up to a time t, the $Dose_\alpha^{asy,0D}(RnPo;r)$ calculated in equation (17) is optionally multiplied by $$1 - e^{\frac{-t}{\tau_{Ra}}}.$$

The spatial dependence of the dose is governed by the $^{220}$Rn diffusion length:

$$L_{Rn} = \sqrt{\frac{D_{Rn}}{\lambda_{Rn} - \lambda_{Ra}}} \quad (18)$$

For the dose contributed by $^{212}$Bi and $^{212}$Po, we first define the diffusion lengths of $^{212}$Pb and $^{212}$Bi:

$$L_{Pb} = \sqrt{\frac{D_{Pb}}{\lambda_{Pb} + \alpha_{Pb} - \lambda_{Ra}}} \quad (19)$$

$$L_{Bi} = \sqrt{\frac{D_{Bi}}{\lambda_{Bi} + \alpha_{Bi} - \lambda_{Ra}}} \quad (20)$$

In some embodiments, the effective $^{212}$Pb lifetime is:

$$\tau_{Pb}^{eff} = \frac{1}{\lambda_{Pb} + \alpha_{Pb}} \quad (21)$$

This parameter is essentially a geometric average of the mean radioactive lifetime of $^{212}$Pb, $\tau_{Pb}=1/\lambda_{Pb}$ and its mean clearance time $1/\alpha_{Pb}$.

The asymptotic $^{212}$Bi/$^{212}$Po alpha particle dose for a point source is given by:

$$Dose_\alpha^{asy,0D}(BiPo; r) = \frac{\lambda_{Bi} E_\alpha(BiPo)}{\rho} \left( A_{Bi} \frac{e^{-r/L_{Rn}}}{r} + B_{Bi} \frac{e^{-r/L_{Pb}}}{r} + C_{Bi} \frac{e^{-r/L_{Bi}}}{r} \right) \left( \tau_{Ra} - \tau_{Pb}^{eff} \right) \quad (22)$$

where:

$$A_{Pb} = \left( \frac{L_{Rn}^2 L_{Pb}^2}{L_{Rn}^2 - L_{Pb}^2} \right) \frac{\lambda_{Rn}}{D_{Pb}} \frac{P_{des}(Rn) \Gamma_{Ra}^{src}(0)}{4\pi D_{Rn}} \quad (23)$$

$$B_{Pb} = \frac{(P_{des}^{eff}(Pb) - P_{des}(Rn)) \Gamma_{Ra}^{src}(0)}{4\pi D_{Pb}} - A_{Pb} \quad (24)$$

$$(25)$$

$$A_{Bi} = \left( \frac{L_{Rn}^2 L_{Bi}^2}{L_{Rn}^2 - L_{Bi}^2} \right) \frac{\lambda_{Pb}}{D_{Bi}} A_{Pb} \quad (26)$$

$$B_{Bi} = \left( \frac{L_{Pb}^2 L_{Bi}^2}{L_{Pb}^2 - L_{Bi}^2} \right) \frac{\lambda_{Pb}}{D_{Bi}} B_{Pb}$$

$$(27)$$

$$C_{Bi} = -(A_{Bi} + B_{Bi})$$

To calculate an approximate dose up to a time t, the following equation is used to calculate $Dose_\alpha^{asy,0D}(BiPo;r)$ instead of equation (22):

$$Dose_\alpha^{asy,0D}(BiPo; r) = \qquad (22')$$

$$\frac{\lambda_{Bi} E_\alpha(BiPo)}{\rho}\left(A_{Bi}\frac{e^{-\frac{r}{L_{Rn}}}}{r} + B_{Bi}\frac{e^{-\frac{r}{L_{Pb}}}}{r} + C_{Bi}\frac{e^{-\frac{r}{L_{Bi}}}}{r}\right)$$

$$\left(\tau_{Ra}\left(1-e^{-\frac{t}{\tau_{Ra}}}\right) - \tau_{Pd}^{eff}\left(1-e^{-\frac{t}{\tau_{Pb}^{eff}}}\right)\right)$$

In some embodiments the physical source can be approximated as a finite line source. In this case, the total alpha particle dose D(r,θ,t) at any point (defined by r and θ relative to the source center and axis) is obtained by dividing the source to a large number of small point-like segments and summing the contributions of $^{220}$Rn/$^{216}$Po and $^{212}$Bi/$^{212}$Pb, equations (17) and (22), from each segment, using the radial distances from the point (r,θ) to each segment.

The total radiation dose D(r,θ,t) due to alpha particles at any point is the sum of contributions by the pairs $^{220}$Rn/$^{216}$Po and $^{212}$Bi/$^{212}$Pb, equations (17) and (22).

Experimentally, it is more convenient to replace $\alpha_{Pb}$ by an equivalent parameter, namely the $^{212}$Pb leakage probability, defined as:

$$P_{leak}(Pb) = \frac{\alpha_{Pb}}{\lambda_{Pb} + \alpha_{Pb}}$$

In some embodiments, the diffusion length $L_{Pb}$ of $^{212}$Pb is measured in mice-borne tumors and accordingly the diffusion coefficient $D_{Pb}$ is set using equation (19). Measurements carried out by applicant, found values of the diffusion length $L_{Pb}$ in the range of about 0.2-0.7 millimeters. The values differ among tumor types and/or distance between the source and the tumor perimeter.

The values for several types of tumors are listed in the following table.

| Tumor type | 212Pb diffusion length in millimeters |
|---|---|
| Squamous cell carcinoma | 0.50 ± 0.12 |
| Colon | 0.45 ± 0.06 |
| GBM | 0.40 ± 0.09 |
| Prostate | 0.35 ± 0.05 |
| Breast (triple negative) | 0.35 ± 0.05 |
| Pancreas | 0.30 ± 0.08 |

Accordingly, in some embodiments, in calculating the radionuclide distributions, the diffusion length $L_{Pb}$ of $^{212}$Pb is given the average value in the table of the corresponding tumor type. Alternatively, the lower value of the corresponding range in the table is used. In some embodiments, for cancer types not in the table, a value smaller than 0.4 mm, smaller than 0.35 mm or even smaller than 0.3 mm is used for the diffusion length $L_{Pb}$.

Optionally, the $^{220}$Rn diffusion length is estimated in the range 0.2-0.4 mm, for example, by a value of at least 0.23 millimeters, at least 0.25 mm, or even at least 0.27 mm. In some embodiments, a value of 0.3 mm is used for the $^{220}$Rn diffusion length. Alternatively or additionally, the $^{220}$Rn diffusion length used is smaller than 0.33 mm, smaller than 0.29 millimeters or even smaller than 0.27 millimeters.

The $^{212}$Pb leakage probability is optionally estimated by a probability greater than 30% or even greater than 35%, for example 40%. Optionally, the $^{212}$Pb leakage probability is assumed to be lower than 70%, lower than 60% or even lower than 50%. In some embodiments, different values of the $^{212}$Pb leakage probability are used for different regions of the tumor. The value for regions close to the edge of the tumor is optionally greater than 70% or even greater than 80%. Deep inside the tumor, in its necrotic core, the $^{212}$Pb leakage probability can be much lower, e.g., less than 10%.

It is noted that instead of using the integration of equations (15)-(16) to calculate the radiation dose from the radionuclide distributions, other calculation methods may be used, such as Monte Carlo techniques.

Table Generation

The tables are generated from the total alpha particle dose D(r,θ,t) of each point from the beginning of the procedure (e.g., insertion of the sources to the tumor) at time t=0, up to time t. In some embodiments, instead of inserting the calculated radiation distribution values D(r,θ,t) directly into tables, the calculated distribution values D(r,θ,t) are converted into a form accepted by a commercially available radiation treatment planning system (TPS), which in turn generates the tables.

Optionally, the tables are generated by a treatment planning system (TPS), such as the BrachyVision TPS, which is based on the functions:

$$\dot{D}_{TPS}(r,\theta,t) = \dot{D}_{TPS}(r,\theta,0)e^{-\lambda t}$$

$$D_{TPS}(r,\theta,t) = \int_0^t \dot{D}_{TPS}(r,\theta,t')dt' = \dot{D}_{TPS}(r,\theta,0)\tau(1-e^{-t/\tau}),$$

where $\tau = \frac{1}{\lambda}$ $$\dot{D}_{TPS}(r,\theta,0) = Sk(0)\Lambda\frac{G_L(r,\theta)}{G_L(r_0,\theta_0)}g_L(r)F(r,\theta)$$

and requires user setting of the functions $g_L(r)$ and $F(r,\theta)$, an activity level of the sources, a dose rate constant Λ per table, and a value $f_{ak}$, which is a conversion factor between activity and Air Kerma Strength. This formalism is described, for example, in the TG-43 publication mentioned in the background section, and which is incorporated herein by reference in its entirety. It is noted that such a TPS is not designed for alpha radiation.

In accordance with some embodiments, the value of $f_{ak}$ is set arbitrarily, for example to 1, and the $g_L(r)$ and $F(r,\theta)$ functions are calculated for a given time t from the DaRT radiation distribution values D(r,θ,t) as:

$$g_L^{(t)}(r) = \frac{D(r,\theta_0,t)}{D(r_0,\theta_0,t)}\frac{G_L(r_0,\theta_0)}{G_L(r,\theta_0)}$$

$$F^{(t)}(r,\theta) = \frac{D(r,\theta,t)}{D(r,\theta_0,t)}\frac{G_L(r,\theta_0)}{G_L(r,\theta)}$$

where $G_L(\ )$ is a general closed-form geometrical function, which depends on the source length L and is already programmed in the TPS. The parameters $r_0$ and $\theta_0$ represent a particular reference point (e.g., $r_0$=1 cm and $\theta_0$=90°). The dose rate constant Λ is assigned for each table a calibration value suitable for that table. Note that unlike conventional brachytherapy sources, the functions F( ) and $g_L(\ )$ for DaRT depend on the duration of the treatment t, because of temporal changes in the spatial shape of the number densities of the diffusing atoms.

For cases in which the TPS limits the value of F( ), instead of using F( ), a normalized $$F_{norm} = \frac{F(r, \theta)}{Fmax}$$

is used, where Fmax is selected as a highest value of the function F( ), or a sufficient value which prevents $F_{norm}$ from going beyond the bounds allowed by the TPS. The value of $F_{max}$ is optionally compensated for, if not internally compensated for by the TPS, in setting the TPS system coefficient $\Lambda_{TPS} = \Lambda F_{max}$.

Optionally, $r_0$ is selected to prevent g(r) from going out the bounds of the values allowed by the TPS. The values of Sk(0),Λ are optionally selected such that $$Sk(0)\Lambda = \frac{D(r_0, \theta_0, t)}{r(1 - e^{-t/\tau_{Ra}})},$$

where $\tau_{Ra}$ is the mean lifetime of $^{224}$Ra.

Electron and Photon Radiation

In some embodiments, separate tables are prepared for the alpha radiation and for the electron and photon radiation. In calculating the radiation dose distribution, separate calculations are performed for the alpha radiation by accessing alpha radiation tables and for the electron and photon radiation by accessing suitable tables and then the results are combined. Optionally, the electron and/or photon radiation tables provide accumulated dose values, as provided by the alpha-radiation tables. Alternatively, the electron and/or photon radiation tables provide dose rate values, as in the TG-43 publication mentioned above.

Alternatively, a single table is used for the alpha, electron and photon radiation. Optionally, in accordance with this alternative, in summing the alpha, electron and/or photon radiation, the alpha radiation value or the electron and/or photon radiation value is multiplied by user provided relative biological effectiveness (RBE) factors, determined using any suitable method known in the art, which take into account the different biological effects of the alpha and electron and/or photon radiation. RBE values for alpha particles depend on the type of the tumor, and are typically in the range 3-5. For electrons and photons RBE values are typically 1 at high energy (above a few hundred keV), but become larger than 1 at lower energies.

Optionally, in calculating the electron and/or radiation dose, for simplicity, the radionuclides are all assumed to be located on the source, and the migration of radionuclides in the tumor is ignored. This assumption was found to have only a small effect on the results, because of the long range of electrons and large mean free path of gamma and x-ray photons relative to the migration scale, governed by the diffusion lengths. In some embodiments, however, the electron and/or photon radiation dose calculation does take into account the early removal of radionuclides through the blood stream, for example by reducing the number of $^{212}$Pb radionuclides in the tumor by the $^{212}$Pb leakage probability.

Optionally, the electron and photon radiation dose is calculated by Monte Carlo techniques (e.g., using the EGS, FLUKA, GEANT4, MCNP or track structure codes), for the entire spectrum of emitted radiation by $^{224}$Ra and its daughters. Optionally, for simplicity, the medium is assumed to be water. Alternatively, other calculation methods are used, such as model based dose calculation algorithms (MBDCAs).

Alternatives

In the above description, the tumor is considered to have the same parameters throughout its volume. In other embodiments, the tumor is considered to have different parameter values in different areas. Optionally, separate tables are generated for different distances of the sources from an edge of the tumor. For example, separate calculations are performed for sources in a range up to 2 millimeters from an edge of the tumor, between 2-4 millimeters from the edge of the tumor, between 4-6 millimeters from the edge of the tumor, and above 6 millimeters from the edge of the tumor. In other embodiments, more than 4 ranges of distances of sources from an edge of the tumor are used, and/or ranges of coarser granularities than 2 millimeters, or finer granularities than 2 millimeters, are used.

For each of the ranges, separate values are provided for the tumor parameters. For example, a higher lead-212 leakage probability (and/or a shorter diffusion length) is assigned to areas closer to the tumor edge, as the leakage is higher at the edges of the tumor. In using the tables, for each source a corresponding one of the tables is selected according to the location of the source in the tumor.

The distance between the source and the edge of the tumor is optionally measured from the closest point on the source to the closest point on the edge of the tumor. Alternatively, the distance is measured from the center of the source. Further alternatively the distance is measured as an average distance along the length of the source or an average between the two ends of the source. In other embodiments, in addition to the distance, a measure of an orientation of the source, such as an angle between the source axis and a shortest line connecting the center of the source to an edge of the tumor is used in dividing the tumor into separate zones.

As described above, the same tumor parameters, e.g., diffusion length, are used for the entire duration of the treatment. In other embodiments, however, in the calculation of the radiation dose, one or more of the tumor parameters, such as the diffusion lengths, are changed with the time since the beginning of the treatment, due to the death of cells because of the treatment, which changes the properties of the tumor. It is noted that these embodiments will have a larger effect on calculations of the dose during longer term periods, than during short term durations in which the parameters of the tumor change very little or not at all.

Alternatively to using tables, the above calculation methods are used directly for calculation of the radiation dose distribution.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

APPENDIX

The underlying assumptions of the DL model are:

The migration of atoms inside the tumor is governed by diffusion.

The tissue is homogeneous, isotropic, and time-independent, and thus the diffusion coefficients are constant.

It is sufficient to model the migration of $^{220}$Rn, $^{212}$Pb and $^{212}$Bi. $^{216}$Po, $^{212}$Po and $^{208}$Tl are in local secular equilibrium with their respective parent isotopes (with suitable branching ratios for the latter two).

$^{212}$Pb migration can be described using a single effective diffusion coefficient.

$^{212}$Pb atoms reaching major blood vessels are trapped in red blood cells and are then immediately cleared from the tumor. This is represented by a single constant sink term.

$^{212}$Rn atoms do not form chemical bonds and are very short-lived, and therefore the equation for Rn does not include a sink term.

The equation for $^{212}$Bi does contain a sink term, but it is considered a second-order effect and generally set to zero.

We consider the case of a cylindrical source of radius $R_0$, and length l along the z axis, and assume axial symmetry. Under the above assumptions, in cylindrical coordinates (r,z) the equations describing the dynamics of the main daughter atoms in the decay chain . . . $^{220}$Rn, $^{212}$Pb and $^{212}$Bi . . . are:

$$\frac{\partial n_{Rn}}{\partial t} = D_{Rn}\left(\frac{1}{r}\frac{\partial}{\partial r}\left(r\frac{\partial n_{Rn}}{\partial r}\right) + \frac{\partial^2 n_{Rn}}{\partial z^2}\right) - \lambda_{Rn}n_{Rn} \quad (1)$$

$$\frac{\partial n_{Pb}}{\partial t} = D_{Pb}\left(\frac{1}{r}\frac{\partial}{\partial r}\left(r\frac{\partial n_{Pb}}{\partial r}\right) + \frac{\partial^2 n_{Pb}}{\partial z^2}\right) + \lambda_{Rn}n_{Rn} - (\lambda_{Pb} + \alpha_{Pb})n_{Pb} \quad (2)$$

$$\frac{\partial n_{Bi}}{\partial t} = D_{Bi}\left(\frac{1}{r}\frac{\partial}{\partial r}\left(r\frac{\partial n_{Bi}}{\partial r}\right) + \frac{\partial^2 n_{Bi}}{\partial z^2}\right) + \lambda_{Pb}n_{Pb} - (\lambda_{Bi} + \alpha_{Bi})n_{Bi} \quad (3)$$

where $n_{Rn}$, $n_{Pb}$, $n_{Bi}$, $D_{Rn}$, $D_{Pb}$, $D_{Bi}$ and $\lambda_{Rn}$, $\lambda_{Pb}$, $\lambda_{Bi}$ are the number densities, diffusion coefficients and decay rate constants of $^{220}$Rn, $^{212}$Pb and $^{212}$Bi, respectively. $\alpha_{Pb}$ and $\alpha_{Bi}$ are the leakage rate constants, accounting for clearance through the blood, of $^{212}$Pb and $^{212}$Bi. One can generally assume $\alpha_{Bi}=0$, as will be done here. The boundary conditions, for $r \to R_0$ and $|z| \leq l/2$ (z=0 at the seed mid plane), are:

$$\lim_{r \to R_0} 2\pi r j_{Rn}(r, z, t) = P_{des}(Rn)\frac{\Gamma_{Ra}^{src}(0)}{l}e^{-\lambda_{Ra}t} \quad (4)$$

$$\lim_{r \to R_0} 2\pi r j_{Pb}(r, z, t) = \left(P_{des}^{eff}(Pb) - P_{des}(Rn)\right)\frac{\Gamma_{Ra}^{src}(0)}{l}e^{-\lambda_{Ra}t} \quad (5)$$

$$\lim_{r \to R_0} 2\pi r j_{Pb}(r, z, t) = 0 \quad (6)$$

where $j_x = -D_z \partial n_x / \partial r$, with x representing $^{220}$Rn, $^{212}$Pb and $^{212}$Bi. $\Gamma_{Ra}^{src}(0)$ is the initial $^{224}$Ra activity on the source (assumed to be uniform) and $\lambda_{Ra}$ is the $^{224}$Ra decay rate constant. $P_{des}(Rn)$ and $P_{des}^{eff}(Pb)$ are the desorption probabilities of $^{220}$Rn and $^{212}$Pb, respectively, representing the probability that a decay of a $^{224}$Ra on the source will lead to the emission of either a $^{220}$Rn or $^{212}$Pb atom into the tumor; we use the term "effective" for $P_{des}^{eff}(Pb)$, because it includes several emission pathways. For $|z|>l/2$, $\lim_{r \to R_0} r j_x(r,z,t)=0$ for the three isotopes.

The solution for equations (1-3) provides the number densities $n_{Rn}(r,z,t)$, $n_{Pb}(r,z,t)$ and $n_{Bi}(r,z,t)$. The alpha dose is calculated under the assumption that the range of alpha particles is much smaller than the dominant diffusion length of the problem (see below). The dose from source insertion to time t is comprised of two contributions: one arising from the summed alpha particle energy of the pair $^{220}$Rn+$^{216}$Po, and the other from the alpha decay of either $^{212}$Bi or $^{212}$Po:

$$Dose_\alpha(RnPo; r, z, t) = \frac{E_\alpha(RnPo)}{\rho}\int_0^t \lambda_{Rn}n_{Rn}(r, z, t')dt' \quad (7)$$

$$Dose_\alpha(BiPo; r, z, t) = \frac{E_\alpha(BiPo)}{\rho}\int_0^t \lambda_{Bi}n_{Bi}(r, z, t')dt' \quad (8)$$

where $E_\alpha(RnPo)=(6.288+6.778)$ MeV=13.066 MeV is the total alpha particle energy of $^{220}$Rn and $^{216}$Po, $E_\alpha(BiPo)=$ 7.804 MeV is the weighted-average energy of the alpha particles emitted by $^{212}$Bi and $^{212}$Po, and $\rho$ is the tissue density. In what follows, we define the "asymptotic dose" as the dose delivered from source insertion to infinity—in practice, over several weeks.

The spread of $^{220}$Rn, $^{212}$Pb and $^{212}$Bi is governed by their respective diffusion lengths, defined as:

$$L_{Rn} = \sqrt{\frac{D_{Rn}}{\lambda_{Rn} - \lambda_{Ra}}} \quad (9)$$

$$L_{Pb} = \sqrt{\frac{D_{Pb}}{\lambda_{Pb} + \alpha_{Pb} - \lambda_{Ra}}} \quad (10)$$

$$L_{Bi} = \sqrt{\frac{D_{Pb}}{\lambda_{Bi} + \alpha_{Bi} - \lambda_{Ra}}} \quad (11)$$

The diffusion length is a gross measure of the average displacement of an atom from its creation site, to the point of its decay or clearance by the blood. For a point source the radial dependence of the number densities and alpha dose components comprises terms proportional to $e^{-r/L_x}/(r/L_x)$. Typical ranges are $L_{Rn} \sim 0.2$-$0.4$ mm, $L_{Pb} \sim 0.3$-$0.7$ mm and $L_{Bi}/L_{Pb} \sim 0.1$-$0.2$.

Another important parameter is the $^{212}$Pb leakage probability $P_{leak}(Pb)$, defined as the probability that a $^{212}$Pb atom released from the source is cleared from the tumor by the blood before its decay. The leakage probability therefore reflects the competition between $^{212}$Pb radioactive decay and clearance through the blood, such that:

$$P_{leak}(Pb) = \frac{\alpha_{Pd}}{\lambda_{Pb} + \alpha_{Pb}} \qquad (12)$$

The typical range of values is $P_{leak}(Pb) \sim 0.2$-$0.8$.

At long times after source insertion into the tumor the number densities reach an asymptotic form: $n_x^{asy}(r,z,t) = \bar{n}_x(r,z)e^{-\lambda_{Rn}t}$. For $^{220}$Rn this condition is satisfied within several minutes throughout the tumor, while for $^{212}$Pb and $^{212}$Bi the asymptotic form is attained within a few days, depending on the distance from the source.

The closed-form asymptotic solution of the DL model equations for an infinitely long cylindrical source are as follows. For $^{220}$Rn we get:

$$n_{Rn}^{asy}(r, t) = A_{Rn} K_0\left(\frac{r}{L_{Rn}}\right) e^{-\lambda_{Ra}t} \qquad (13)$$

where:

$$A_{Rn} = \frac{P_{des}(Rn)(\Gamma_{Ra}^{src}(0)/l)}{2\pi D_{Rn}(R_0/L_{Rn}) K_1(R_0/L_{Rn})} \qquad (14)$$

In these expressions $K_0(\xi)$ and $K_1(\xi)$ are modified Bessel functions of the second kind:

$$K_0(\xi) = \int_0^\infty \frac{\cos(\xi t)}{\sqrt{t^2+1}} dt \qquad (15)$$

$$K_1(\xi) = -\frac{dK_0}{d\xi} \qquad (16)$$

$K_0(r/L)$ is a steeply-falling function, and is the cylindrical analogue to $\exp(-r/L)/(r/L)$ appearing in expressions for the number densities and dose of the point source. For $^{212}$Pb we have:

$$n_{Pb}^{asy}(r, t) = \left(A_{Pb} K_0\left(\frac{r}{L_{Rn}}\right) + B_{Pb} K_0\left(\frac{r}{L_{Pb}}\right)\right) e^{-\lambda_{Ra}t} \qquad (17)$$

where:

$$A_{Pb} = \frac{L_{Rn}^2 L_{Pb}^2}{L_{Rn}^2 - L_{Pb}^2} \frac{\lambda_{Rn}}{D_{Pb}} A_{Rn} \qquad (18)$$

$$B_{Pb} = \frac{(P_{des}^{eff}(Pb) - P_{des}(Rn))(\Gamma_{Ra}^{src}(0)/l)}{2\pi D_{Pb}(R_0/L_{Pb}) K_1(R_0/L_{Pb})} - A_{Pb} \frac{(R_0/L_{Rn}) K_1(R_0/L_{Rn})}{(R_0/L_{Pb}) K_1(R_0/L_{Pb})} \qquad (19)$$

Finally, for $^{212}$Bi we get:

$$n_{Bi}^{asy}(r, t) = \left(A_{Bi} K_0\left(\frac{r}{L_{Rn}}\right) + B_{Bi} K_0\left(\frac{r}{L_{Pb}}\right) + C_{Bi} K_0\left(\frac{r}{L_{Bi}}\right)\right) e^{-\lambda_{Ra}t} \qquad (20)$$

where:

$$A_{Bi} = \frac{L_{Rn}^2 L_{Bi}^2}{L_{Rn}^2 - L_{Bi}^2} \frac{\lambda_{Pb}}{D_{Bi}} A_{Pb} \qquad (21)$$

$$B_{Bi} = \frac{L_{Pb}^2 L_{Bi}^2}{L_{Pb}^2 - L_{Bi}^2} \frac{\lambda_{Pb}}{D_{Bi}} B_{Pb} \qquad (22)$$

$$C_{Bi} = -\frac{(R_0/L_{Rn}) K_1(R_0/L_{Rn}) A_{Bi} + (R_0/L_{Pb}) K_1(R_0/L_{Pb}) B_{Bi}}{(R_0/L_{Bi}) K_1(R_0/L_{Bi})} \qquad (23)$$

The expressions above can also describe the limit of an infinite line source in the limit $R_0/L_x \to 0$.

To approximately account for the buildup stage of the solution, one can assume that it is uniform throughout the tumor, i.e., independent of the distance from the source. Under this "0D" temporal approximation, for a point source and adapted here for the cylindrical case, one can write:

$$n_{Rn}^{0D}(r, t) = A_{Rn} K_0\left(\frac{r}{L_{Rn}}\right)\left(e^{-\lambda_{Ra}t} - e^{-\lambda_{Rn}t}\right) \qquad (24)$$

and $$n_{Bi}^{0D}(r, t) = \left(A_{Bi} K_0\left(\frac{r}{L_{Rn}}\right) + B_{Bi} K_0\left(\frac{r}{L_{Pb}}\right) + C_{Bi} K_0\left(\frac{r}{L_{Bi}}\right)\right)\left(e^{-\lambda_{Ra}t} - e^{-(\lambda_{Pt}+\alpha_{Pb})t}\right) \qquad (25)$$

Under this approximation, the asymptotic alpha dose components are:

$$Dose_\alpha^{asy}(RnPo; r) = \frac{E_\alpha(RnPo)}{\rho} \lambda_{Rn} A_{Rn} K_0\left(\frac{r}{L_{Rn}}\right)(\tau_{Ra} - \tau_{Rn}) \qquad (26)$$

$$Dose_\alpha^{asy}(BiPo; r) = \frac{E_\alpha(RnPo)}{\rho} \lambda_{Bi} \left(A_{Bi} K_0\left(\frac{r}{L_{Rn}}\right) + B_{Bi} K_0\left(\frac{r}{L_{Pb}}\right) + C_{Bi} K_0\left(\frac{r}{L_{Bi}}\right)\right)(\tau_{Ra} - \tau_{Pb}^{eff}) \qquad (27)$$

where $\tau_{Ra} = 1/\lambda_{Ra}$, $\tau_{Rn} = 1/\lambda_{Rn}$ and $\tau_{Pb}^{eff} = 1/(\lambda_{Pb}+\alpha_{Pb})$. The error introduced by the 0D approximation is of the order of the ratio between mean lifetimes of $^{220}$Rn and $^{212}$Pb and that of $^{224}$Ra, i.e. $\tau_{Rn}/\tau_{Ra} \sim 10^{-4}$ and $\tau_{Pb}/\tau_{Ra} \sim 0.1$, respectively.

A complete time-dependent solution to the DL model can be done numerically using a finite-element approach. For the one-dimensional case, i.e., infinite cylindrical or line source along the z axis, we solve equations (1-3) setting $\partial^2 n_x/\partial z^2 = 0$. The solution therefore depends solely on the radial coordinate r. We divide our domain into concentric cylindrical shells, enumerated $i = 1 \ldots N_r$, of equal radial width $\Delta r$. The radius of the source is $R_0$; we choose $\Delta r$ such that $R_0/\Delta r$ is an integer number, and $\Delta r$ is considerably smaller than $L_{Rn}$ and $L_{Pb}$ ($L_{Bi}$ has a negligible effect on the solution and therefore should not constrain $\Delta r$). The central radius of the i-th shell is:

$$r_i = R_0 + (i - \tfrac{1}{2})\Delta r \qquad (28)$$

We employ a fully implicit scheme, thereby assuring the solution is stable. The time steps are changed adaptively according to the relative change in the solution between the current step and the previous one, as explained below.

The average number densities in the i-th shell are $n_{Rn,i}$, $n_{Pb,i}$, and $n_{Bi,i}$. We enumerate the time steps by p. For shells away from the source surface, with $1 < i \leq N_r$, the DL model equations take the discrete implicit form:

$$\frac{n_{x,i}^{(p+1)} - n_{x,i}^{(p)}}{\Delta t} = D_x \left(\frac{n_{x,i+1}^{(p+1)} + n_{x,i-1}^{(p+1)} - 2n_{x,i}^{(p+1)}}{\Delta r^2} + \frac{1}{r_i}\frac{n_{x,i+1}^{(p+1)} - n_{x,i-1}^{(p+1)}}{2\Delta r}\right) - (\lambda_x - \alpha_x) n_{x,i}^{(p+1)} + s_{x,i}^{(p+1)} \qquad (29)$$

where x stands for Rn, Pb and Bi and $\alpha_{Rn} = 0$. Outside our domain we set the number densities to zero, such that in eq. (29) for $i = N_r$, $n_{x,i+1} = 0$.

For the $i = 1$ shell, immediately outside of the source, using the boundary conditions, eq. (4)-(6), gives:

$$\frac{n_{x,i}^{(p+1)} - n_{x,i}^{(p)}}{\Delta t} = \frac{D_x}{\Delta r^2}\left(\frac{1 + \Delta r/R_0}{1 + \Delta r/2R_0}\right)\left(n_{x,2}^{(p+1)} - n_{x,1}^{(p+1)}\right) - \qquad (30)$$

The source terms $s_{x,i}^{p+1}$ appearing in eq. (29) and (30) are:

$$s_{Rn,i}^{p+1} = \frac{P_{des}(R_n)(\Gamma_{Ra}^{src}(0)/l)e^{-\lambda_{Ra}t_{p+1}}}{2\pi R_0 \Delta r(1 + \Delta r/2R_0)} \sigma_{i,1} \quad (31)$$

$$s_{Pb,i}^{p+1} = \frac{(P_{des}^{eff}(Pb) - P_{des}(Rn))(\Gamma_{Rn}^{src}(0)/l)e^{-\lambda_{Ra}t_{p+1}}}{2\pi R_0 \Delta r(1 + \Delta r/2R_0)} \delta_{i,1} + \lambda_{Rn} n_{Rn,i}^{p+1} \quad (32)$$

$$s_{Bi,i}^{p+1} = \lambda_{Pb} n_{Pb,i}^{p+1} \quad (33)$$

where $\delta_{i,1}=1$ for i=1 and zero otherwise. Rearranging eq. (29) and (30), we get the general form:

$$n_{x,i}^{(p)} + s_{x,i}^{(p+1)}\Delta t = A_{i,i-1}^{(x)} n_{x,i-1}^{(p+1)} + A_{i,i}^{(x)} n_{x,i}^{(p+1)} + A_{i,i+1}^{(x)} n_{x,i+1}^{(p+1)} \quad (34)$$

The matrix coefficients introduced in eq. (34) depend on the value of i, reflecting the boundary conditions for i=1 and i=$N_r$. Retaining terms up to first order in $\Delta r/r_i$ the different cases are summarized below:

$$A_{i,i-1}^{(x)} = -\frac{D_x \Delta t}{\Delta r^2}\left(1 - \frac{\Delta r}{2r_i}\right) \quad (35)$$
$$1 < i \le N_r$$

$$A_{i,i}^{(x)} = 1 + \frac{D_x \Delta t}{\Delta r^2}\left(1 + \frac{\Delta r}{2r_i}\right) + (\lambda_x + \alpha_x)\Delta t \quad i = 1 \quad (36)$$
$$= 1 + \frac{2D_x \Delta t}{\Delta r^2} + (\lambda_x + \alpha_x)\Delta t \quad 1 < i \le N_r$$

$$A_{i,i+1}^{(x)} = -\frac{D_x \Delta t}{\Delta r^2}\left(1 + \frac{\Delta r}{2r_i}\right) \quad (37)$$
$$1 \le i < N_r$$

with $r_i$ given in eq. (28). Writing eq. (34) in matrix form:

$$\begin{pmatrix} n_{x,1}^{(p)} \\ n_{x,2}^{(p)} \\ \vdots \\ n_{x,i}^{(p)} \\ \vdots \\ n_{x,N_r-1}^{(p)} \\ n_{x,N_r}^{(p)} \end{pmatrix} + \begin{pmatrix} s_{x,1}^{(p)} \\ s_{x,2}^{(p)} \\ \vdots \\ s_{x,i}^{(p)} \\ \vdots \\ s_{x,N_r-1}^{(p)} \\ s_{x,N_r}^{(p)} \end{pmatrix} \Delta t_{p+1} = \quad (38)$$

$$\begin{pmatrix} A_{1,1}^{(x)} & A_{1,1}^{(x)} & 0 & \cdots & & & 0 \\ A_{2,1}^{(x)} & A_{2,2}^{(x)} & A_{2,3}^{(x)} & 0 & \cdots & & 0 \\ & \ddots & \ddots & \ddots & & & \\ \vdots & 0 & A_{i,i-1}^{(x)} & A_{i,i}^{(x)} & A_{i,i+1}^{(x)} & 0 & \vdots \\ & & & \ddots & \ddots & \ddots & \\ 0 & \cdots & & 0 & A_{N_r-1,N_r-2}^{(x)} & A_{N_r-1,N_r-1}^{(x)} & A_{N_r-1,N_r}^{(x)} \\ 0 & & & \cdots & 0 & A_{N_r,N_r-1}^{(x)} & A_{N_r,N_r}^{(x)} \end{pmatrix}$$

$$\begin{pmatrix} n_{x,1}^{(p+1)} \\ n_{x,2}^{(p+1)} \\ \vdots \\ n_{x,i}^{(p+1)} \\ \vdots \\ n_{x,N_r-1}^{(p+1)} \\ n_{x,N_r}^{(p+1)} \end{pmatrix}$$

which can be written as $n_x^{(p)} + s_x^{(p+1)}\Delta t = A_x n_x^{(p+1)}$. Multiplying on the left by the inverse of $A_x$, we get:

$$n_x^{(p+1)} = A_x^{-1}(n_x^{(p)} + s_x^{(p+1)}\Delta t), \quad (39)$$

which completes the solution for the p+1 step. Note that although the source terms are calculated for the p+1 step they are, in fact, known when the matrix equations are solved. The reason is that in the p+1 step we first solve for $^{220}$Rn, then for $^{212}$Pb and lastly for $^{212}$Bi. The source term for $^{220}$Rn depends only on time, those of $^{212}$Pb are found using the p+1 solution for $^{220}$Rn, and those of $^{212}$Bi—using the p+1 solution for $^{212}$Pb. Another point to take into account is that since $\Delta t$ is changed along the calculation and the matrix coefficients depend on $\Delta t$, they must be updated accordingly in each step.

The alpha dose components are also updated in each step:

$$Dose_\alpha^{(p+1)}(RnPo; i) = Dose_\alpha^{(p)}(RnPo; i) + \frac{E_\alpha(RnPo)}{\rho}\lambda_{Rn} n_{Rn,i}^{(p+1)}\Delta t \quad (40)$$

$$Dose_\alpha^{(p+1)}(BiPo; i) = Dose_\alpha^{(p)}(BiPo; i) + \frac{E_\alpha(BiPo)}{\rho}\lambda_{Bi} n_{Bi,i}^{(p+1)}\Delta t \quad (41)$$

At the end of the p+1 step, $\Delta t$ is updated based on the relative change in the solution. This can be done in a number of ways. A particular choice, implemented here, was to consider the relative change in the total dose (sum of the RnPo and BiPo contributions) at a particular point of interest $r_{i_0}$ (e.g., at 2 mm):

$$\Delta t_{new} = \Delta t \cdot \frac{\epsilon_{tol}}{\left(Dose_\alpha^{(p+1)}(tot; i_0) - Dose_\alpha^{(p)}(tot; i_0)\right)/Dose_\alpha^{(p)}(tot; i_0)} \quad (42)$$

where $\epsilon_{tol}$ is a preset tolerance parameter. For practicality, one can further set upper and lower limits on $\Delta t$ to balance between calculation time and accuracy. Although the initial time step should be small compared to $^{220}$Rn half-life, its particular value has little effect on the accuracy of the calculated asymptotic dose.

The finite-element scheme described above was implemented in MATLAB in a code named "DART1D". The solution of eq. (39), the critical part of the calculation, was done using a tridiagonal matrix solver employing the Thomas algorithm. The use of this solver was found to be ~4 times faster than MATLAB's mldivide ('\') tool, which was, in turn, about 3-fold faster than inverting the matrix using inv (A). The code was found to converge to sub-percent level for a modest choice of the discretization parameter values. For example, setting $\epsilon_{tol}=10^{-2}$, $\Delta r=0.02$ mm, and $\Delta t_0=0.1$ s (for a domain radius $R_{max}=7$ mm and a treatment duration of 30 d) resulted, with a run-time of ~0.5 s, in doses which were ~0.5% away from those obtained with $\epsilon_{tol}=10^{-4}$, $\Delta r=0.01$ mm and $\Delta t_0=0.1$ s, with a run-time of ~3 min (both on a modern laptop (computer with an Intel i7 processor and 16 GB RAM memory). The latter, more accurate run, was within $7 \cdot 10^{-4}$ of the 0D approximation for the $^{220}$Rn+$^{216}$Po dose.

Figure 4A:
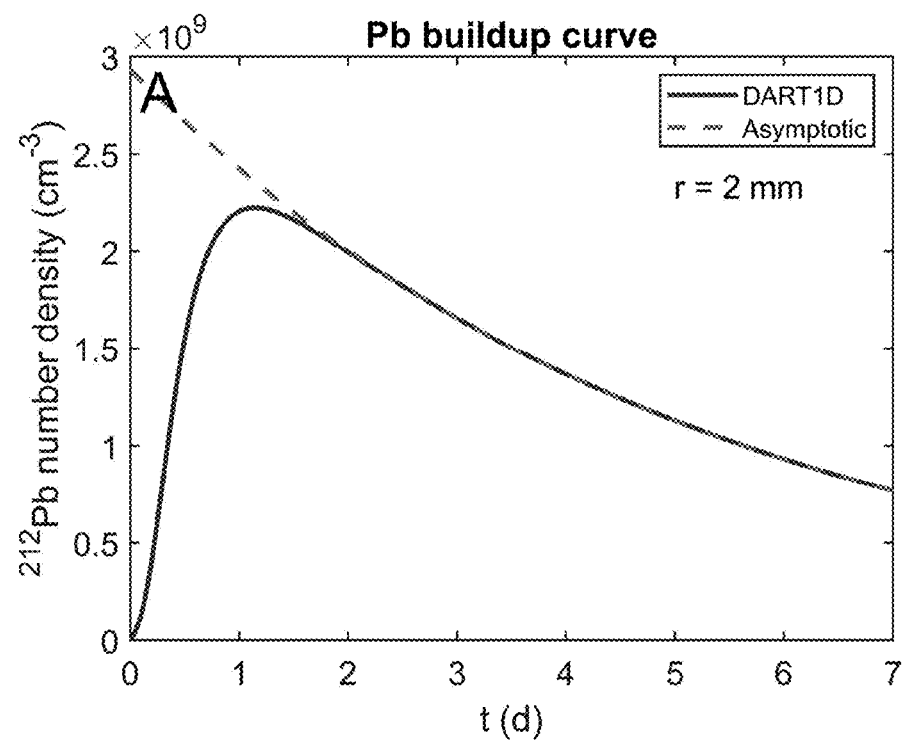
FIG. 4A is a graph showing a comparison between a DART1D solution and an asymptotic solution for the $^{212}$Pb number density 2 mm from the source.
Figure 4B:
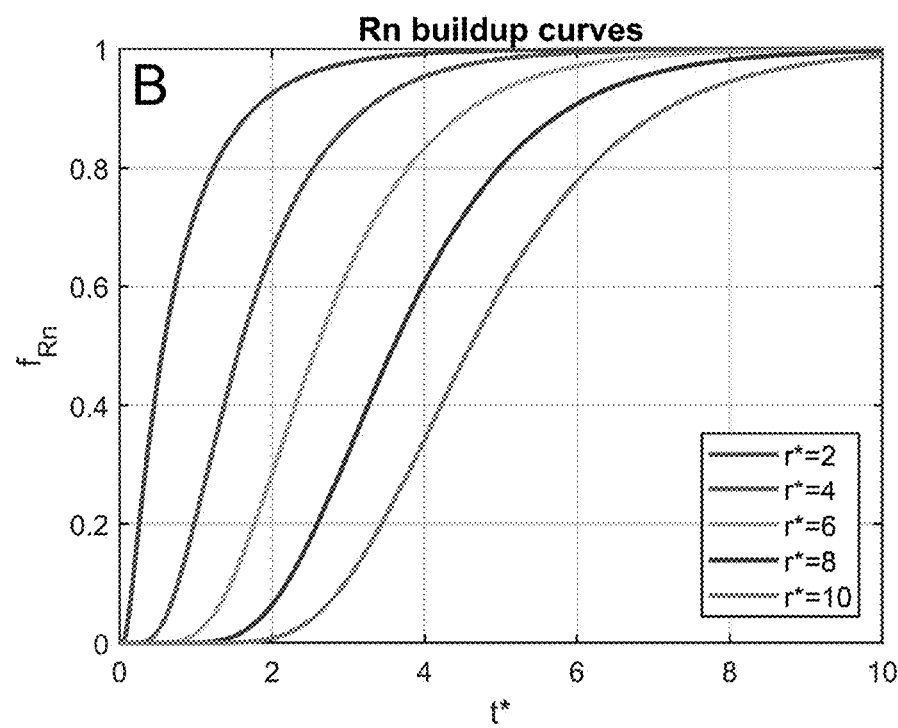
FIG. 4B is a graph showing a ratio between the DART1D and asymptotic solutions of the $^{220}$Rn number density at various distances from the source axis.

FIGS. 4 and 5 examine several aspects of the numerical solution. FIG. 4 shows the DART1D solution in comparison with the asymptotic expressions eq. (13) and (17). On the left we show the DART1D time-dependent $^{212}$Pb number density at a distance of 2 mm from the source, along with the corresponding asymptotic solution. On the right, we show the ratio between the numerical and asymptotic solutions for $^{220}$Rn, $f_{Rn} \equiv n_{Rn}/n_{Rn}^{\alpha,sy}$, plotted for varying distances from the source. The distances are given in units of the $^{220}$Rn diffusion length, $r^* \partial r/L_{Rn}$, and the time in units of $1/(\lambda_{Rn}-\lambda_{Ra})$ which is roughly the mean $^{220}$Rn lifetime, $t^* \partial(\lambda_{Rn}-\lambda_{Ra})t$. The numerical solutions converge to the asymptotic ones with a delay that increases with the distance from the source. For $^{220}$Rn this occurs on the scale of minutes, while for $^{212}$Pb over a few days. The adaptive time step allows DART1D to handle both transients efficiently.

Figure 5A:
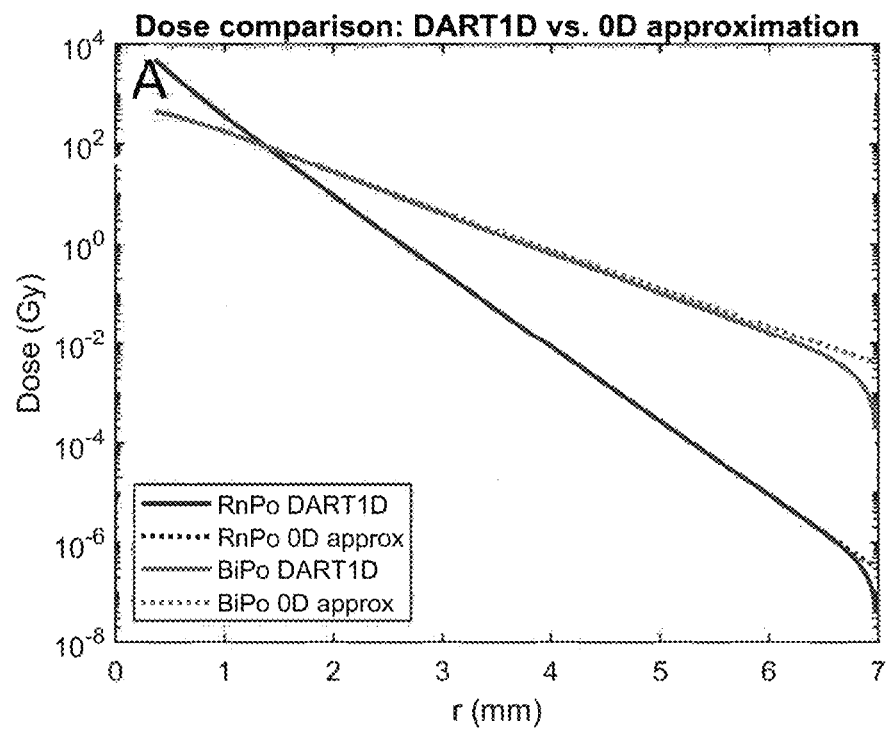
FIG. 5A is a graph showing a comparison of dose values between the DART1D $^{220}$Rn+$^{216}$Po and $^{220}$Bi/$^{220}$Po alpha doses and the 0D approximation for an infinite cylindrical source.
Figure 5B:
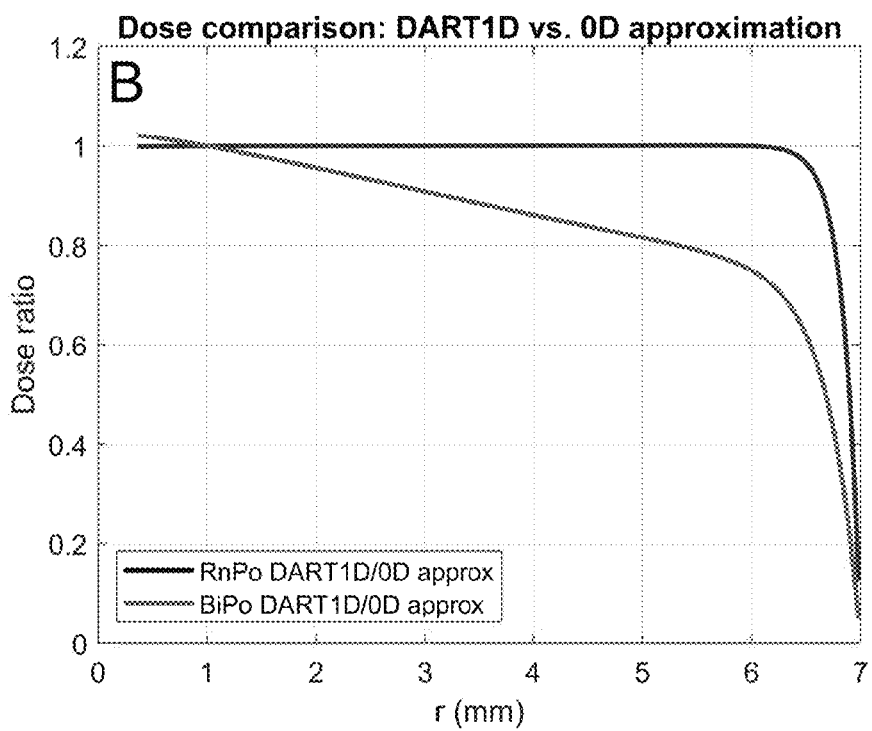
FIG. 5B is a graph showing approximation ratios of the DART1D $^{220}$Rn+$^{216}$Po and $^{220}$Bi/$^{220}$Po alpha doses and the 0D approximation for an infinite cylindrical source.

FIG. 5A shows the DART1D $^{220}$Rn+$^{216}$Po and $^{212}$Bi/$^{212}$Po alpha dose components calculated for the case $L_{Rn}=0.3$ mm, $L_{Pb}=0.6$ mm, $L_{Bi}=0.1 L_{Pb}$, $\alpha_{Pb}=\lambda_{Pb}$ (i.e., $P_{leak}$(Pb)=0.5), and $\alpha_{Bi}=0$. The source radius is $R_0=0.35$ mm, the $^{224}$Ra activity is 3 µCi/cm and the desorption probabilities are $P_{des}$(Rn)=0.45 and $P_{des}^{eff}$(Pb)=0.55. The dose components are given at t=30 d post treatment. The numerical calculation is compared to the 0D approximations, eq. (26) and (27). The assumption of zero number density outside the calculation domain results in a departure from the expected solution about two diffusion lengths away from the boundary: ~0.5 mm for $^{220}$Rn and ~1 mm for $^{212}$Bi and $^{212}$Po, whose spatial distribution is governed by the $^{212}$Pb diffusion length. This indicates that the radial extent of the calculation domain should be about 10 times larger than the largest diffusion length of the problem. FIG. 5B shows the ratio between the DART1D-calculated dose components and the corresponding 0D approximations. Except for the edge effect at $r \rightarrow R_{max}$, the numerical solution for $^{220}$Rn+$^{216}$Po coincides with the 0D approximation to better than $1 \cdot 10^{-3}$ for $\epsilon_{tol}=10^{-4}$, $\Delta r=0.01$ mm and $\Delta t_0=0.1$ s up to r~5 mm. For $^{212}$Bi/$^{212}$Po the 0D approximation underestimates the dose at r<1 mm and overestimates it at larger distances because of the increasing delay in buildup of $^{212}$Pb as a function of r. The error is ~5-10% at therapeutically relevant distances from the source (around 2-3 mm).

We move now to two dimensions to treat a cylindrical source ("seed") of radius $R_0$ and finite length l. The source lies along the z axis with z=0 at its mid plane. We solve the DL equations over a cylindrical domain extending from r=0 to r=$R_{max}$ and from z=$-Z_{max}$ to z=$+Z_{max}$. Both $R_{max}$ and $Z_{max}-l/2$ should be much larger than the largest diffusion length of the problem. The domain comprises ring elements of equal radial width $\Delta r$ and equal z-width $\Delta z$. We choose $\Delta r$ and $\Delta z$ such that $R_0/\Delta r$ and $l/(2\Delta z)$ are integer numbers, with $\Delta r$ and $\Delta z$ much smaller than $L_{Rn}$ and $L_{Pb}$. We enumerate the rings by i,j, where i=1 ... $N_r$ and j=1 ... $N_z$. Elements with i=1 are on-axis, while j=1 at the bottom of the cylindrical domain, and j=$N_z$ at the top. Unlike the 1D case, where the source is infinitely long and we only consider points with r>$R_0$, for a finite seed in 2D we must also solve the equations for points above and below the seed, with r<$R_0$ and |z|>½l. As for the 1D case, the radius and z-coordinate of the i,j ring, $r_i, z_j$, are defined at the center of its rz cross section. For the innermost i=1 rings $r_1$=½$\Delta r$. Points inside the seed, i.e., in rings with $r_i \leq R_0-\Delta r/2$, and $|z_j| \leq \frac{1}{2}l-\frac{1}{2}\Delta z$, have zero number densities of $^{220}$Rn, $^{212}$Pb and $^{212}$Bi.

Discretization of eq. (1-3) in 2D yields, for interior ring elements in the cylindrical domain (outside of the seed and not touching its wall or bases, and with i>1):

$$\frac{n_{x,i,j}^{(p+1)} - n_{x,i,j}^{(p)}}{\Delta t} = D_x \left( \frac{n_{x,i+1,j}^{(p+1)} + n_{x,i-1,j}^{(p+1)} - 2n_{x,i,j}^{(p+1)}}{\Delta r^2} + \frac{1}{r_i} \frac{n_{x,i+1,j}^{(p+1)} - n_{x,i-1,j}^{(p+1)}}{2\Delta r} + \frac{n_{x,i,j+1}^{(p+1)} + n_{x,i,j-1}^{(p+1)} - 2n_{x,i,j}^{(p+1)}}{\Delta z^2} \right) - (\lambda_x + \alpha_x) n_{x,i,j}^{(p+1)} + s_{x,i,j}^{(p+1)} \quad (43)$$

Eq. (43) holds also for ring elements on the external surfaces of the domain, with i=$N_r$, j=1 or j=$N_z$, as the number densities for rings with i=$N_r$+1, j=0 or j=$N_z$+1 are all zero. For ring elements on-axis (i=1), above or below the seed, we require $(\partial n_x/\partial r)_{r=0}=0$. Since the $^{224}$Ra activity is confined to the seed wall, the z-component of the current density is set to zero on the seed bases. i.e., $(\partial n_x/\partial z)_{z=\pm l/2}=0$. Defining $i_s$ as the radial index of ring elements touching the seed wall (i.e., $r_{i_s}=R_0+\Delta r/2$), for ring elements with $|z_j| \leq l/2-\Delta z/2$, eq. (43) becomes, similarly to the 1D case:

$$\frac{n_{x,i_s,j}^{(p+1)} - n_{x,i_s,j}^{(p)}}{\Delta t} = \frac{D_x}{\Delta r^2} \left( \frac{1+\Delta r/R_0}{1+\Delta r/2R_0} \right) \left( n_{x,i_s+1,j}^{(p+1)} - n_{x,i_s,j}^{(p+1)} \right) + \frac{D_x}{\Delta z^2} \left( n_{x,i_s,j+1}^{(p+1)} + n_{x,i_s,j-1}^{(p+1)} - 2n_{x,i_s,j}^{(p+1)} \right) - (\lambda_s + \alpha_x) n_{x,i_s,j}^{(p+1)} + s_{x,i_s,j}^{(p+1)} \quad (44)$$

The source terms in eq. (43) and (44) are similar to the 1D case, with the additional requirement that $|z_j|<l/2$:

$$s_{Rn,i,j}^{(p+1)} = \frac{P_{des}(Rn)(\Gamma_{Ra}^{des}(0)/l)e^{-\lambda_{Ra} t_{p+i}}}{2\pi R_0 \Delta r (1+\Delta r/2R_0)} \delta_{i,i_s} \cdot \left( \frac{1-\text{sign}(|z_j|-l/2)}{2} \right) \quad (45)$$

$$s_{Pb,i,j}^{p+1} = \frac{(P_{des}^{eff}(Pb) - P_{des}(Rn))(\Gamma_{Ra}^{src}(0)/l)e^{-\lambda_{Ra} t_{p+1}}}{2\pi R_0 \Delta r (1+\Delta r/2R_0)} \delta_{i,i_s} \cdot \left( \frac{1-\text{sign}(|z_j|-l/2)}{2} \right) + \lambda_{Rn} n_{Rn,i,j}^{p+1} \quad (46)$$

$$s_{Bi,i,j}^{p+1} = \lambda_{Pb} n_{Pb,i,j}^{p+1} \quad (47)$$

In order to solve eq. (43) in matrix form we use linear indexing. We rearrange the 2D elements $n_{x,i,j}^{(p)}$ and $s_{x,i,j}^{(p)}$ in two column vectors $\tilde{n}_x^{(p)}$ and $\tilde{s}_x^{(p)}$ in sequential order. We define:

$$k(i,j)=(j-1)N_r+i \quad (48)$$

$$\tilde{n}_{x,k}^{(p)}=n_{x,i,j}^{(p)} \quad (49)$$

$$\tilde{s}_{x,k}^{(p)}=s_{x,i,j}^{(p)} \quad (50)$$

with k=1 ... $N_r N_z$. Noting that $n_{x,i\pm 1,j}^{(p)}=\tilde{n}_{x,k\pm 1}^{(p)}$ and $n_{x,i,j\pm 1}^{(p)}=\tilde{n}_{x,k\pm N_r}^{(p)}$, eq. (43) can be rearranged as:

$$\tilde{n}_{x,k}^{(p)}+\tilde{s}_{x,k}^{(p+1)}\Delta t = M_{k,k-N_r}^{(x)}\tilde{n}_{x,k-N_r}^{(p+1)}+M_{k,k-1}^{(x)} \tilde{n}_{x,k-1}^{(p+1)}+M_{k,k}^{(x)}\tilde{n}_{x,k}^{(p+1)}+M_{k,k+1}^{(x)}\tilde{n}_{x,k+1}^{(p+1)}+ M_{k,k+N_r}^{(x)}\tilde{n}_{x,k+N_r}^{(p+1)} \quad (51)$$

As for the 1D case, the matrix elements appearing in eq. (51) depend on the values of i,j (and therefore k), in a manner that satisfies the boundary conditions. For compactness, we define the following intermediate quantities:

$$K_z^{(x)} = \frac{D_x \Delta t}{\Delta z^2} \tag{52}$$

$$K_r^{(x)} = \frac{D_x \Delta t}{\Delta r^2} \tag{53}$$

$$K_r^{(x+)} = \frac{D_x \Delta t}{\Delta r^2}\left(1 + \frac{\Delta r}{2r_i}\right) \tag{54}$$

$$K_r^{(x-)} = \frac{D_x \Delta t}{\Delta r^2}\left(1 - \frac{\Delta r}{2r_i}\right) \tag{55}$$

-continued $$S_1^{(x)} = 1 + 2K_r^{(x)} + K_z^{(x)} + (\lambda_x + \alpha_x)\Delta t \tag{56}$$

$$S_2^{(x)} = 1 + 2K_r^{(x)} + 2K_z^{(x)} + (\lambda_x + \alpha_x)\Delta t \tag{57}$$

$$S_+^{(x)} = 1 + K_r^{(x+)} + 2K_z^{(x)} + (\lambda_x + \alpha_x)\Delta t \tag{58}$$

Table 1 lists the expressions for the matrix elements $M_{k,l}^{(x)}$ for all possible cases for $r_i$ and $z_j$. With these, we can write eq. (51) in matrix form (with $K \equiv N_r N_z$):

TABLE 1

Matrix elements in 2D.

| Case | $M_{k,k-N_r}^{(x)}$ | $M_{k,k-1}^{(x)}$ | $M_{k,k}^{(x)}$ | $M_{k,k+1}^{(x)}$ | $M_{k,k+N_r}^{(x)}$ |
|---|---|---|---|---|---|
| $R_0 + \frac{\Delta r}{2} < r_i < R_{max} - \frac{\Delta r}{2}$ & $\|z_j\| < Z_{max} - \frac{\Delta z}{2}$ | $-K_z^{(x)}$ | $-K_r^{(x-)}$ | $S_2^{(x)}$ | $-K_r^{(x+)}$ | $-K_z^{(x)}$ |
| $\frac{\Delta r}{2} < r_i \leq R_0 + \frac{\Delta r}{2}$ & $\frac{l}{2} + \frac{\Delta z}{2} < \|z_j\| < Z_{max} - \frac{\Delta z}{2}$ | $-K_z^{(x)}$ | $-K_r^{(x-)}$ | $S_2^{(x)}$ | $-K_r^{(x+)}$ | $-K_z^{(x)}$ |
| $r_i = R_0 + \frac{\Delta r}{2}$ & $\|z_j\| = \frac{l}{2} + \frac{\Delta z}{2}$ | $-K_z^{(x)}$ | $-K_r^{(x-)}$ | $S_2^{(x)}$ | $-K_r^{(x+)}$ | $-K_z^{(x)}$ |
| $r_i = R_0 + \frac{\Delta r}{2}$ & $\|z_j\| < \frac{l}{2}$ | $-K_z^{(x)}$ | 0 | $S_+^{(x)}$ | $-K_r^{(x+)}$ | $-K_z^{(x)}$ |
| $\frac{\Delta r}{2} < r_i < R_0$ & $z_j = \frac{l}{2} + \frac{\Delta z}{2}$ | 0 | $-K_r^{(x-)}$ | $S_1^{(x)}$ | $-K_r^{(x+)}$ | $-K_z^{(x)}$ |
| $\frac{\Delta r}{2} < r_i < R_0$ & $z_j = -\frac{l}{2} - \frac{\Delta z}{2}$ | $-K_z^{(x)}$ | $-K_r^{(x-)}$ | $S_1^{(x)}$ | $-K_r^{(x+)}$ | 0 |
| $r_i = \frac{\Delta r}{2}$ & $\frac{l}{2} + \frac{\Delta z}{2} < \|z_j\| < Z_{max} - \frac{\Delta z}{2}$ | $-K_z^{(x)}$ | 0 | $S_2^{(x)}$ | $-K_r^{(x+)}$ | $-K_z^{(x)}$ |
| $r_i = R_{max} - \frac{\Delta r}{2}$ & $\|z_j\| < Z_{max} - \frac{\Delta z}{2}$ | $-K_z^{(x)}$ | $-K_r^{(x-)}$ | $S_2^{(x)}$ | 0 | $-K_z^{(x)}$ |
| $\frac{\Delta r}{2} < r_i < R_{max} - \frac{\Delta r}{2}$ & $z_j = Z_{max} - \frac{\Delta z}{2}$ | $-K_z^{(x)}$ | $-K_r^{(x-)}$ | $S_2^{(x)}$ | $-K_r^{(x+)}$ | 0 |
| $\frac{\Delta r}{2} < r_i < R_{max} - \frac{\Delta r}{2}$ & $z_j = -Z_{max} + \frac{\Delta z}{2}$ | 0 | $-K_r^{(x-)}$ | $S_2^{(x)}$ | $-K_r^{(x+)}$ | $-K_z^{(x)}$ |
| $r_i = \frac{\Delta r}{2}$ & $z_j = Z_{max} - \frac{\Delta z}{2}$ | $-K_z^{(x)}$ | 0 | $S_2^{(x)}$ | $-K_r^{(x+)}$ | 0 |
| $r_i = \frac{\Delta r}{2}$ & $z_j = -Z_{max} + \frac{\Delta z}{2}$ | 0 | 0 | $S_2^{(x)}$ | $-K_r^{(x+)}$ | $-K_z^{(x)}$ |
| $r_i = \frac{\Delta r}{2}$ & $z_j = \frac{l}{2} + \frac{\Delta z}{2}$ | 0 | 0 | $S_2^{(x)}$ | $-K_r^{(x+)}$ | $-K_z^{(x)}$ |
| $r_i = \frac{\Delta r}{2}$ & $z_j = -\frac{l}{2} - \frac{\Delta z}{2}$ | $-K_z^{(x)}$ | 0 | $S_2^{(x)}$ | $-K_r^{(x+)}$ | 0 |
| $r_i = R_{max} - \frac{\Delta r}{2}$ & $z_j = Z_{max} - \frac{\Delta z}{2}$ | $-K_z^{(x)}$ | $-K_r^{(x-)}$ | $S_2^{(x)}$ | 0 | 0 |
| $r_i = R_{max} - \frac{\Delta r}{2}$ & $z_j = -Z_{max} + \frac{\Delta z}{2}$ | 0 | $-K_r^{(x-)}$ | $S_2^{(x)}$ | 0 | $-K_z^{(x)}$ |
| $r_i < R_0$ & $\|z_j\| < \frac{l}{2}$ | 0 | 0 | 1 | 0 | 0 |

$$\begin{pmatrix} \tilde{n}_{x,1}^{(p)} \\ \tilde{n}_{x,2}^{(p)} \\ \tilde{n}_{x,3}^{(p)} \\ \vdots \\ \tilde{n}_{x,N_r+2}^{(p)} \\ \tilde{n}_{x,N_r+2}^{(p)} \\ \vdots \\ \tilde{n}_{z,K-1}^{(p)} \\ \tilde{n}_{z,K}^{(p)} \end{pmatrix} + \begin{pmatrix} \tilde{s}_{x,1}^{(p+1)} \\ \tilde{s}_{x,2}^{(p+1)} \\ \tilde{s}_{x,3}^{(p+1)} \\ \vdots \\ \tilde{s}_{x,N_r+1}^{(p+1)} \\ \tilde{s}_{x,N_r+3}^{(p+1)} \\ \vdots \\ \tilde{s}_{z,K-1}^{(p+1)} \\ \tilde{s}_{z,K}^{(p+1)} \end{pmatrix} \Delta t =$$

(59)

$$\begin{pmatrix} M_{1,1}^{(x)} & M_{1,2}^{(x)} & 0 & \ldots & M_{1,1+N_r}^{(x)} & \ldots & & & 0 \\ M_{2,1}^{(x)} & M_{2,2}^{(x)} & M_{2,3}^{(x)} & 0 & \ldots & & & & 0 \\ 0 & M_{3,3}^{(x)} & M_{3,3}^{(x)} & M_{3,4}^{(x)} & 0 & & & & 0 \\ \vdots & & \ddots & \ddots & \ddots & & & & \vdots \\ M_{N_r+2,1}^{(x)} & 0 & \ldots & M_{N_r+1,N_r}^{(x)} & M_{N_r+1,N_r+1}^{(x)} & M_{N_r+1,N_r+2}^{(x)} & 0 & \ldots & 0 \\ 0 & M_{N_r+22}^{(x)} & 0 & \ldots & M_{N_r+2,N_r+1}^{(x)} & M_{N_r+2,N_r+3}^{(x)} & M_{N_r+2,N_r+3}^{(x)} & \ldots & 0 \\ \vdots & & \ddots & & & \ddots & \ddots & \ddots & \vdots \\ 0 & \ldots & 0 & M_{K-1,K-1-N_r}^{(x)} & 0 & \ldots & M_{K-1,K-2}^{(x)} & M_{K-1,K-1}^{(x)} & M_{K-1,K}^{(x)} \\ 0 & & \ldots & 0 & M_{K,K-N_r}^{(x)} & 0 & \ldots & M_{K,K-1}^{(x)} & M_{K,K}^{(x)} \end{pmatrix}$$

$$\begin{pmatrix} \tilde{n}_{x,1}^{(p+1)} \\ \tilde{n}_{x,2}^{(p+1)} \\ \tilde{n}_{x,3}^{(p)} \\ \vdots \\ \tilde{n}_{x,N_r+2}^{(p+1)} \\ \tilde{n}_{x,N_r+2}^{(p+1)} \\ \vdots \\ \tilde{n}_{z,K-1}^{(p+1)} \\ \tilde{n}_{z,K}^{(p+1)} \end{pmatrix}$$

60 or equivalently: $\tilde{n}_x^{(p)} + \tilde{s}_x^{(p+1)}\Delta t = M_x \tilde{n}_x^{(p+1)}$. As for the 1D case, we multiply on the left by the inverse of $M_x$, getting $\tilde{n}_x^{(p+1)} = M_x^{-1}(\tilde{n}_x^{(p)} + \tilde{s}_x^{(p+1)}\Delta t)$. We now run over all possible values of i,j and update $n_{x,i,j}^{(p+1)} = \tilde{n}_{x,k}^{(p+1)}$. Once the new number densities are known in all ring elements, we update the alpha dose components:

$$Dose_\alpha^{(p+1)}(RnPo; i, j) = Dose_\alpha^{(p)}(RnPo; i, j) + \frac{E_\alpha(RnPo)}{\rho} \lambda_{Rn} n_{Rn,i,j}^{(p+1)} \Delta t \quad (60)$$

$$Dose_\alpha^{(p+1)}(BiPo; i, j) = Dose_\alpha^{(p)}(BiPo; i, j) + \frac{E_\alpha(BiPo)}{\rho} \lambda_{Bi} n_{Bi,i,j}^{(p+1)} \Delta t \quad (61)$$

As for the 1D case the time step can be modified in many ways. Here we chose to update it according to the relative change in the overall activity (sum over all isotopes in all ring elements).

The 2D numerical scheme described above was implemented in MATLAB in a code named "DART2D". The code takes roughly 0.5 h to run on a modern laptop (Intel i7 processor with 16 GB RAM) for $\Delta r=0.00.5$ mm, $\Delta z=0.05$ mm, $\epsilon_{tol}=0.01$, $\Delta t_0=0.1$ s, $R_{max}=7$ mm, $Z_{max}=10$ mm and a treatment time of 40 d. The most demanding process is the calculation of $M^{-1}$. Since M is a sparse diagonal matrix, we used MATLAB's spdiags ( ) function, which reduces memory requirements by saving only the diagonal non-zero elements of M, and allows the code to run more efficiently.

Figure 6:
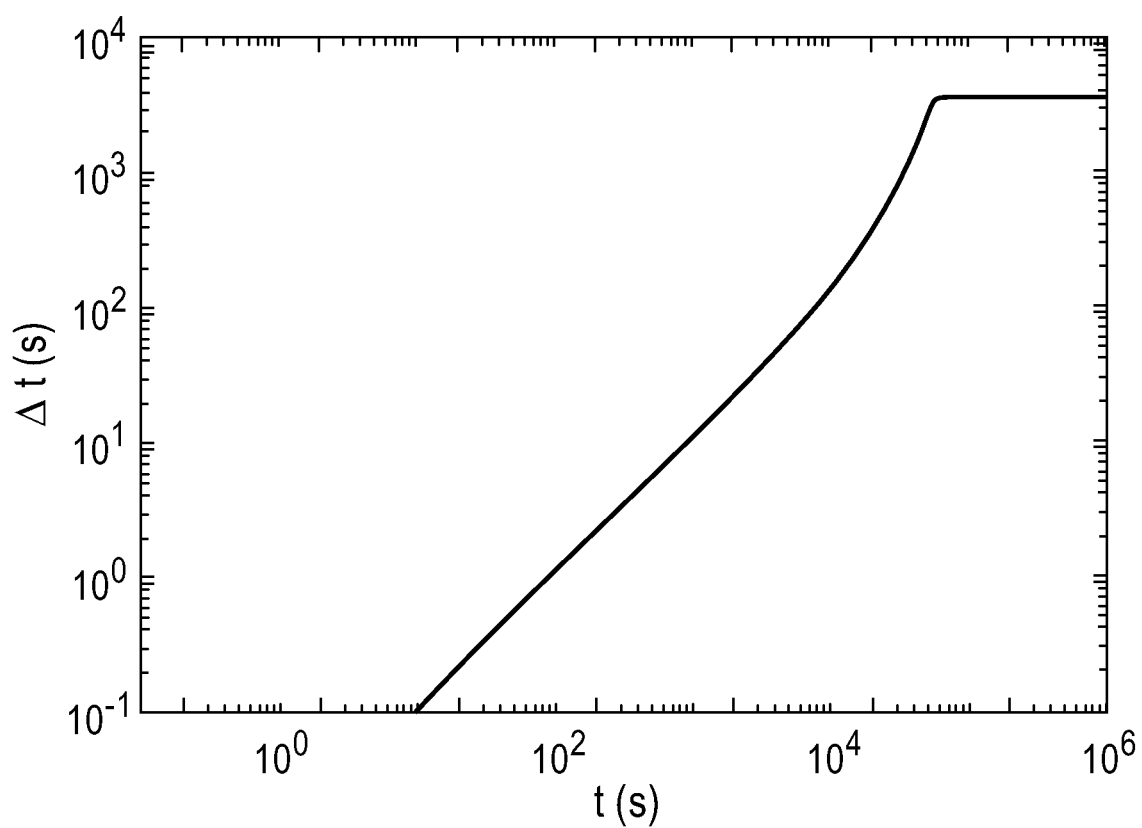
FIG. 6 is a graph showing DART2D variation of time step vs. time.

FIG. 6 shows the dependence of the adaptive time step on time, up to ~11 days. The initial time step is 0.1 s, capturing the $^{220}$Rn buildup with high accuracy (this is also the minimal allowed value for $\Delta t$). It then gradually increases, following the buildup of $^{212}$Pb, eventually reaching its maximal allowed value (here~1 h) in the asymptotic phase driven by $^{224}$Ra decay rate.

The total alpha dose (sum of the $^{220}$Rn+$^{216}$Po and $^{212}$Bi/$^{212}$Po contributions) accumulated over 40 days of DaRT treatment by a seed of finite dimensions is displayed in the rz plane in FIG. 7A. The seed dimensions are $R_0=0.35$ mm and $l=10$ mm. The initial $^{224}$Ra activity of the seed is 3 μCi, with $P_{des}(Rn)=0.45$ and $P_{des}^{eff}(Pb)=0.55$. The other model parameters are: $L_{Pb}=0.6$ mm, $L_{Rn}=0.3$ mm, $L_{Bi}=0.06$ mm, $P_{leak}(Pb)=0.5$, $\alpha_{Bi}=0$. Note that the radial dose profile is nearly unchanged up to ~1.5 mm from the seed end. FIG. 7B shows the dose profiles along r in the seed mid plane and along z parallel to the seed axis, both set such that '0' is the seed edge. The dose along the seed axis is smaller by ~30% near the seed edge, with the difference increasing to a factor of ~3 at 3 mm, compared to that in the mid plane—an important point to consider in treatment planning. Although a similar effect is observed when approximating the seed to a finite line source comprised of point-like segments, this approach leads to significant errors in the dose because it does not consider the finite diameter of the seed, which "pushes" the radial dose to larger values.

Figure 8A:
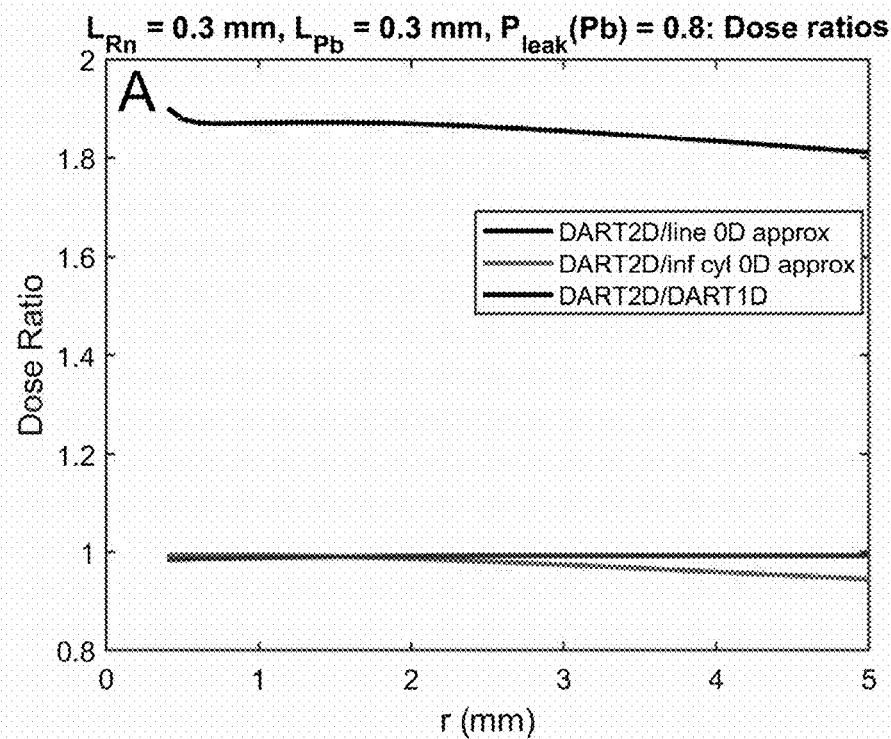
FIG. 8A is a graph showing ratios between the total alpha dose in the seed mid plane calculated by DART2D and those calculated using the 0D line source approximation, the 0D infinite cylinder approximation and the full 1D calculation for an infinite cylindrical source using DART1D, in a low-diffusion, high-leakage case.
Figure 8B:
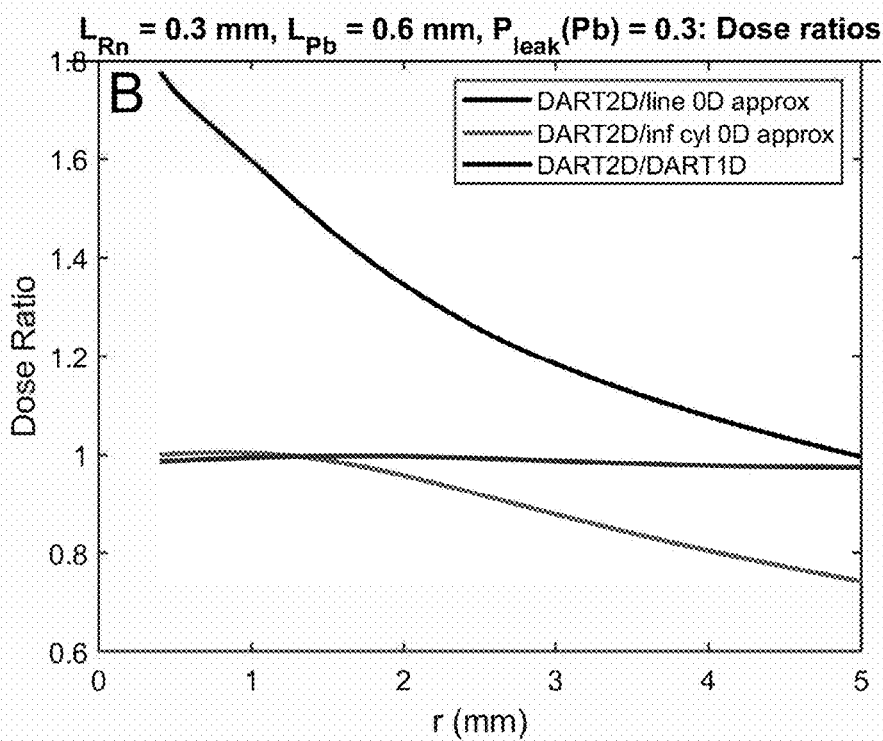
FIG. 8B is a graph showing ratios between the total alpha dose in the seed mid plane calculated by DART2D and those calculated using the 0D line source approximation, the 0D infinite cylinder approximation and the full 1D calculation for an infinite cylindrical source using DART1D, in a high-diffusion, low-leakage case.
Figure 9A:
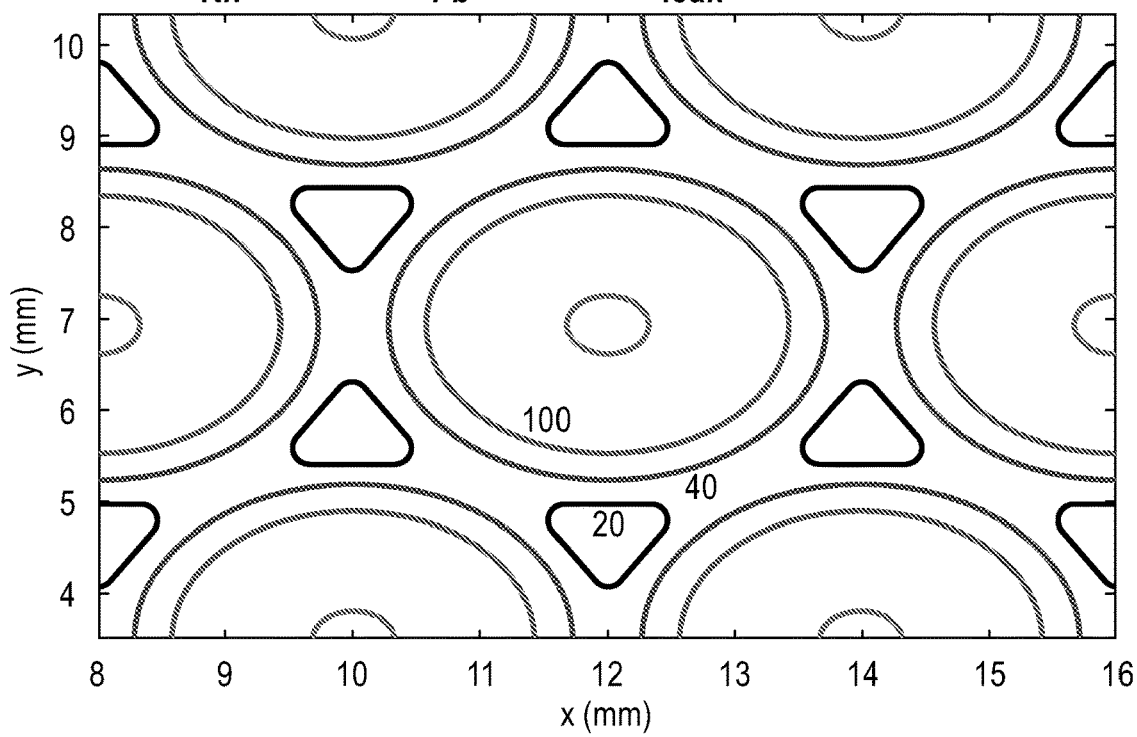
FIG. 9A shows a lattice total alpha dose map comparison for $L_{Rn}$=0.3 mm, $L_{Pb}$=0.3 mm, $P_{leak}$(Pb)=0.8, for line source 0D approximation.
Figure 9B:
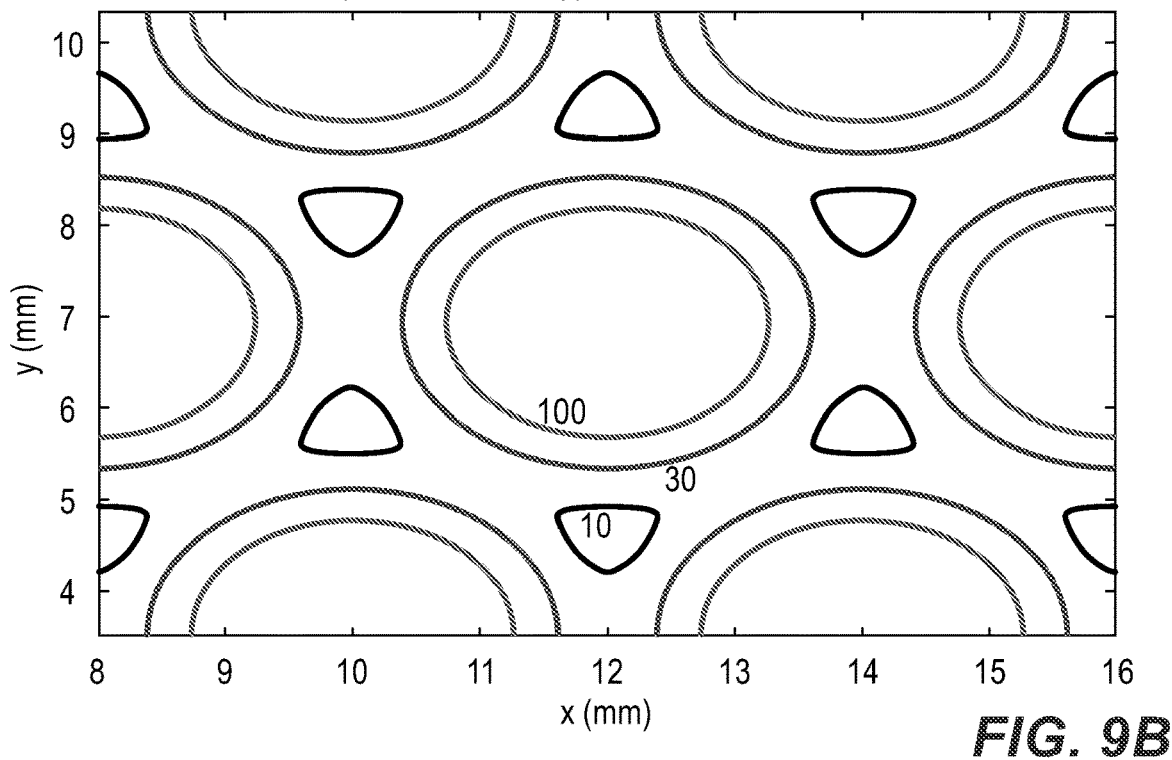
FIG. 9B shows a lattice total alpha dose map comparison for $L_{Rn}$=0.3 mm, $L_{Pb}$=0.6 mm, $P_{leak}$(Pb)=0.3, for line source 0D approximation.
Figure 9C:
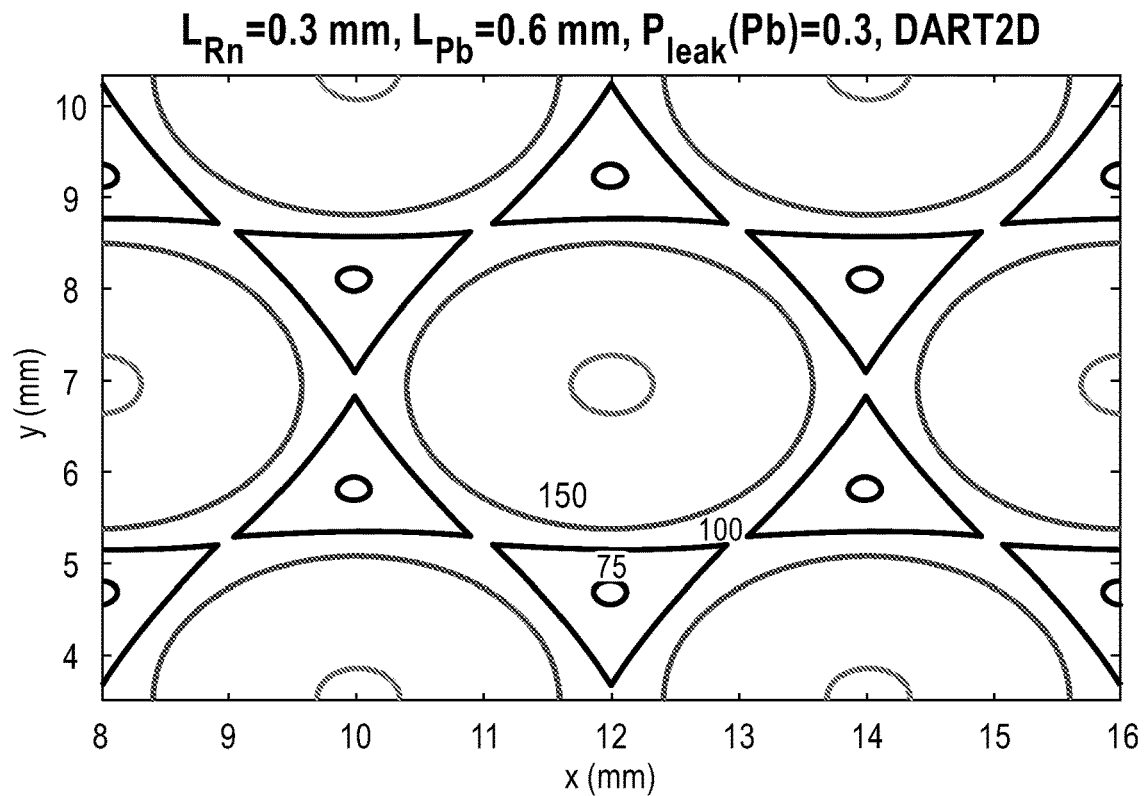
FIG. 9C shows a lattice total alpha dose map comparison for $L_{Rn}$=0.3 mm, $L_{Pb}$=0.3 mm, $P_{leak}$(Pb)=0.8, for full 2D calculation with DART2D.
Figure 9D:
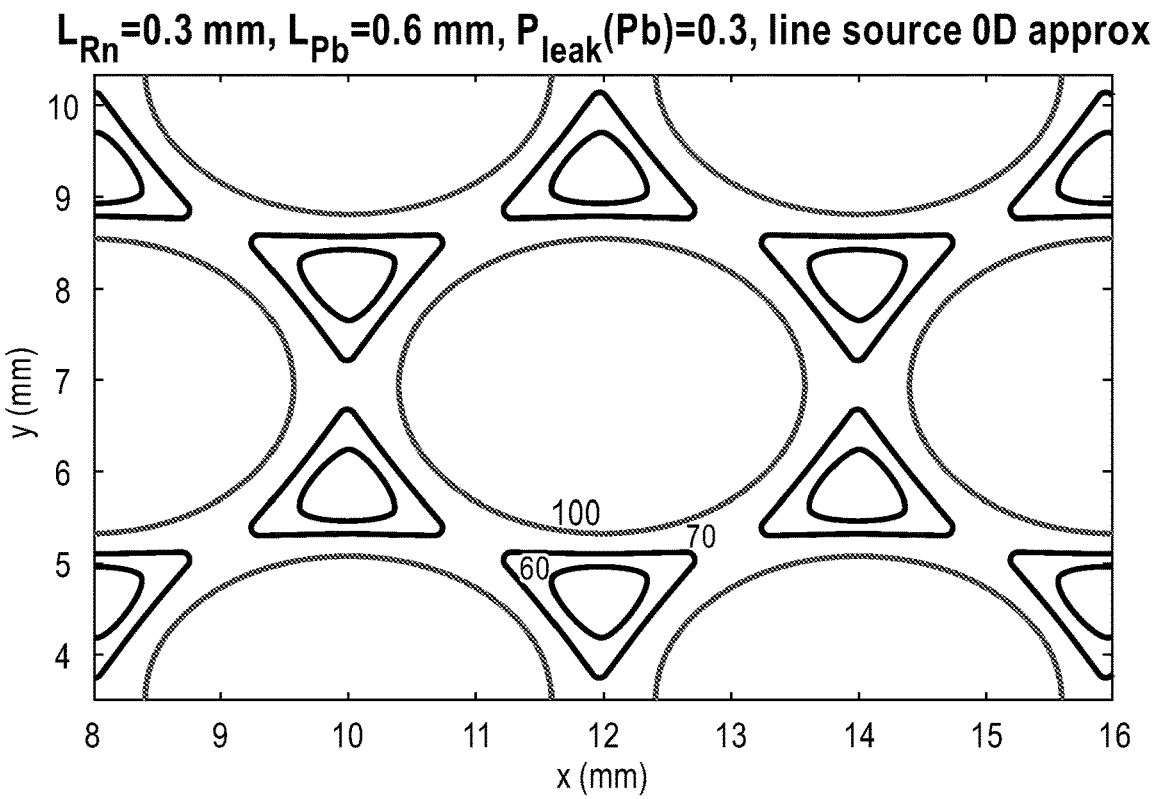
FIG. 9D shows a lattice total alpha dose map comparison for $L_{Rn}$=0.3 mm, $L_{Pb}$=0.6 mm, $P_{leak}$(Pb)=0.3, for line source 0D approximation, for full 2D calculation with DART2D.

We now compare the results of the full 2D calculation with those obtained using either the 0D analytical approximations, or the full 1D calculation. FIG. 8 shows these comparisons of the dose profile calculated in the seed mid planes. On the left we display the comparison for a low-diffusion high-leakage case, with $L_{Rn}=0.3$ mm, $L_{Pb}=0.3$ mm, and $P_{leak}(Pb)=0.8$, and on the right—for a high-diffusion low-leakage case, with $L_{Rn}=0.3$ mm, $L_{Pb}=0.6$ mm, and $P_{leak}(Pb)=0.3$. In both cases $L_{Bi}=0.1L_{Pb}$ and $\alpha_{Bi}=0$. The curves show the ratios between the full 2D calculation with DART2D and those obtained by: (1) approximating the seed to a finite line comprised of point-like segments and using the 0D approximation; (2) using the 0D approximation for an infinite cylindrical source, eq. (26) and (27), and (3) using the full DART1D calculation. Approximating the seed to a finite line source leads to an underestimation of the dose by up to ~80% for both the low- and high-diffusion scenarios. Using the closed-form 0D approximation for a cylindrical source of radius $R_0$ overestimates the dose at 2-3 mm by ~1-2% for the low-diffusion/high-leakage case and ~5-10% for the high-diffusion/low-leakage scenario. In contrast, the full numerical solution (DART1D) for a cylindrical source provides accurate results (on the scale of 0.3%) when compared to the 2D calculation.

FIG. 9 shows the dose calculated for a, hexagonal seed lattice of parallel seeds with a grid spacing of 4 mm. As before, the seed radius is 0.35 mum, its $^{224}$Ra activity is 3 μCi (over 1 cm length), $P_{des}(Rn)=0.45$, $P_{des}^{eff}(Pb)=0.55$. The calculations are for the low-diffusion high-leakage and high-diffusion low-leakage cases defined above. The calculation is done for both the full 2D solution and the 0D line-source approximation. The dose at the mid point between three adjacent seeds is 75/15 Gy for the accurate 2D calculation (high-/low-diffusion, respectively) and 57/8 Gy for the line source approximation, emphasizing the need to consider the finite diameter of the seed.

The invention claimed is:

1. Apparatus for planning a diffusing alpha-emitter radiation therapy (DaRT) treatment session, comprising:
   an output interface;
   a memory configured with a plurality of first tables which provide an accumulated measure of radiation over a specific time period, due to one or more types of DaRT radiotherapy sources which emit daughter radionuclides, for a plurality of different distances and angles relative to the DaRT radiotherapy sources; and
   a processor configured to receive a description of a layout of the DaRT radiotherapy sources in a tumor, to calculate a radiation dose distribution in the tumor responsive to the layout, using the first tables in the memory, and to output feedback for the DaRT treatment session responsive to the radiation dose distribution, through the output interface.

2. The apparatus of claim 1, wherein the memory is additionally configured with a plurality of second tables for different time periods for a single source type, and wherein the processor is configured to determine a treatment duration of the layout, and to select a table from the second tables to be used in calculating the radiation dose distribution responsive to the treatment duration.

3. The apparatus of claim 2, wherein the accumulated measure of radiation provided by the first tables comprises an accumulated radiation dose due only to alpha radiation.

4. The apparatus of claim 1, wherein the memory is additionally configured with a plurality of second tables for a single source type in different zones of the tumor, and wherein the processor is configured to select a table from the second tables to be used in calculating the radiation dose distribution from each DaRT radiotherapy source in the layout, responsive to a zone from the different zones in which the DaRT radiotherapy source is located.

5. The apparatus of claim 4, wherein the processor determines the zone in which the DaRT radiotherapy source is located responsive to a distance between the DaRT radiotherapy source and an edge of the tumor.

6. The apparatus of claim 4, wherein the accumulated measure of radiation provided by the first tables comprises an accumulated radiation dose due to alpha radiation and one or more of electron and photon radiation.

7. The apparatus of claim 1, wherein the processor is configured to identify areas of the tumor having in the calculated radiation dose distribution a radiation dose is-below a threshold and to suggest changes to the layout which bring the radiation dose in the identified areas to above the threshold.

8. The apparatus of claim 1, wherein the processor is configured to repeat the calculation of a radiation dose distribution for a plurality of different treatment durations and to select one of the durations responsive to the calculations.

9. The apparatus of claim 1, wherein the accumulated measure of radiation provided by the first tables comprises one or more number densities of the radionuclides.

10. The apparatus of claim 1, wherein the memory is additionally configured with a plurality of second tables for different tissue types for a single source type, and wherein the processor is configured to determine a tissue type of the tumor, and to select a table from the second tables to be used in calculating the radiation dose distribution responsive to the tissue type.

11. A method of planning a radiotherapy treatment session, comprising:
receiving, by a processor, a description of a layout of a plurality of diffusing alpha-emitter radiation therapy (DaRT) radiotherapy sources in a tumor;
calculating, by the processor, a radiation dose distribution in the tumor responsive to the layout, using tables, wherein each table provides an accumulated measure of radiation over a specific time period, due to a DaRT radiotherapy source of a specific source type from one or more types of DaRT radiotherapy sources which emit daughter radionuclides, for a plurality of different distances and angles relative to the DaRT radiotherapy source; and
outputting from the processor feedback for the treatment session responsive to the radiation dose distribution.

12. The method of claim 11, wherein calculating the radiation dose distribution comprises determining a treatment duration of the layout, and selecting the tables to be used in calculating the radiation dose distribution responsive to the treatment duration.

13. The method of claim 11, wherein calculating the radiation dose distribution comprises selecting the tables to be used in calculating the radiation dose distribution from each source in the layout, responsive to a zone of the tumor in which each source is located.

14. The method of claim 11, comprising repeating the calculation of radiation dose distribution for a plurality of different treatment durations and selecting one of the durations responsive to the calculations.

15. A method of planning a radiotherapy treatment session, comprising:
receiving, by a processor, a plurality of parameters of tissue of a tumor requiring radiotherapy;
receiving, by the processor, an indication of a layout of diffusing alpha-emitter radiation therapy (DaRT) sources to be placed in the tumor;
calculating a distribution of radon-220, lead-212 and bismuth-212 radionuclides in the tumor, responsive to the layout of sources;
determining a first radiation dose distribution resulting from alpha radiation emitted in the tumor, responsive to the calculated distribution;
determining a second radiation dose distribution resulting from electron and photon radiation in the tumor, responsive to the layout of sources;
setting one or more parameters of the radiotherapy treatment session responsive to the determined first and second radiation dose distributions; and
outputting from the processor to a human operator, through an output device, feedback on the radiotherapy treatment session, responsive to the determined first and second radiation dose distributions.

16. The method of claim 15, wherein calculating the distribution of the radionuclides comprises calculating a distribution of the radionuclides for a single source of the sources in the layout and summing the calculated distribution of the radionuclides for the single source, for all of the sources in the layout.

17. The method of claim 16, wherein calculating the distribution of radon-220, lead-212, and bismuth-212 is performed by solving a migration equation of lead-212 including a leakage factor which is a product of a concentration of lead-212 and a constant.

18. The method of claim 15, wherein the setting one or more parameters of the radiotherapy treatment session comprises selecting an activity of the sources in the layout.

19. The method of claim 15, wherein the setting one or more parameters of the radiotherapy treatment session comprises adjusting the layout of the sources.

20. The method of claim 19, wherein calculating the distribution of radon-220, lead-212, and bismuth-212 in the tumor and determining the first radiation dose distribution comprises preparing in advance tables of radiation distributions for a plurality of different tumor types and determining the first radiation dose distribution by summing values matching the layout, from one of the tables.

21. The method of claim 20, wherein calculating the distribution of radon-220, lead-212, and bismuth-212 is performed as a function of diffusion coefficients of radon-220 and lead-212 in the tumor.

22. The method of claim 20, wherein preparing in advance tables of radiation distributions comprises preparing for each of the tumor types, a plurality of tables for respective treatment durations.

23. The method of claim 22, wherein the treatment durations for which the tables are prepared, are unevenly distributed over a duration of effectiveness of the sources of the layout.

24. The method of claim 15, wherein calculating the distribution of radionuclides in the tumor and determining the first radiation dose distribution comprises repeating the calculating of the distribution of radionuclides and the determining of the first radiation dose distribution for a plurality of different durations, and wherein setting one or more parameters of the radiotherapy treatment session comprises selecting a duration of the treatment session responsive to the repeated calculating and determining.

25. The method of claim 24, wherein determining the second radiation dose distribution, is performed in a manner not based on the distribution of radon-220, lead-212, and bismuth-212 in the tumor.

26. The method of claim 24, wherein calculating the distribution of radon-220, lead-212, and bismuth-212 radionuclides comprises calculating based on at least one equation which depends on a diffusion coefficient of lead-212, and wherein the value of the diffusion coefficient of lead-212 is calculated as a function of a diffusion length of lead-212.

27. The method of claim 26, wherein the diffusion length of lead-212 is assigned a value in a range of 0.2-0.4 millimeters.

28. The method of claim 26, wherein the diffusion length of lead-212 is assigned a value dependent on a tissue type of the tumor.

29. The method of claim 15, wherein receiving the indication of the layout comprises receiving an image of the tumor with the sources therein and determining locations of the sources in the tumor responsive to the image.

30. The method of claim 15, wherein calculating the distribution of radon-220, lead-212, and bismuth-212 in the tumor and determining the first radiation dose distribution comprises solving equations numerically using finite elements.

31. The method of claim 30, wherein calculating the distribution of radon-220, lead-212, and bismuth-212 in the tumor and determining the first radiation dose distribution comprises determining a finite element two-dimensional time-dependent solution.

32. The method of claim 30, wherein solving the equations numerically using finite elements comprises solving with boundary conditions for each of the sources both on an outer surface of the sources and on an axis of the sources.

33. The method of claim 30, wherein solving the equations numerically using finite elements comprises solving for a respective cylindrical domain surrounding each of the sources, wherein outside the respective cylindrical domain a number density is set to zero.

* * * * *